(12) United States Patent
Abe et al.

(10) Patent No.: US 8,263,268 B2
(45) Date of Patent: Sep. 11, 2012

(54) ESTER COMPOUND, AND NON-AQUEOUS ELECTROLYTE SOLUTION AND LITHIUM SECONDARY BATTERY EACH USING THE ESTER COMPOUND

(75) Inventors: Koji Abe, Yamaguchi (JP); Chisen Hashimoto, Yamaguchi (JP)

(73) Assignee: UBE Industries, Ltd., Ube-shi (JP)

( * ) Notice: Subject to any disclaimer, the term of this patent is extended or adjusted under 35 U.S.C. 154(b) by 493 days.

(21) Appl. No.: 12/525,207

(22) PCT Filed: Feb. 1, 2008

(86) PCT No.: PCT/JP2008/051653
§ 371 (c)(1),
(2), (4) Date: Jul. 30, 2009

(87) PCT Pub. No.: WO2008/093837
PCT Pub. Date: Aug. 7, 2008

(65) Prior Publication Data
US 2010/0119955 A1    May 13, 2010

(30) Foreign Application Priority Data

Feb. 2, 2007  (JP) .................. 2007-024236
Apr. 25, 2007 (JP) .................. 2007-115135

(51) Int. Cl.
*H01M 6/16* (2006.01)
(52) U.S. Cl. ........ 429/327; 429/307; 429/331; 429/330; 429/199; 429/338; 252/62.2
(58) Field of Classification Search .................. 429/327, 429/307, 331, 330, 199, 338; 252/62.2
See application file for complete search history.

(56) References Cited

FOREIGN PATENT DOCUMENTS

| | | |
|---|---|---|
| EP | 0 645 366 A1 | 3/1995 |
| EP | 1 650 826 A1 | 4/2006 |
| JP | 3 127755 | 5/1991 |
| JP | 8 293323 | 11/1996 |
| JP | 10 308236 | 11/1998 |
| JP | 11 329490 | 11/1999 |
| JP | 2000 119221 | 4/2000 |
| JP | 2000 156243 | 6/2000 |
| JP | 2000 299127 | 10/2000 |
| JP | 2000 323169 | 11/2000 |
| JP | 2000-323169 | * 11/2000 |
| JP | 2006 172950 | 6/2006 |
| JP | 2006 236648 | 9/2006 |

* cited by examiner

*Primary Examiner* — Laura Weiner
(74) *Attorney, Agent, or Firm* — Oblon, Spivak, McClelland, Maier & Neustadt, L.L.P.

(57) ABSTRACT

The present invention includes (1) an ester compound having a specific structure, (2) a nonaqueous electrolytic solution for lithium secondary battery comprising an electrolyte dissolved in a nonaqueous solvent and containing an ester compound having a specific structure in an amount of from 0.01 to 10% by weight of the nonaqueous electrolytic solution, which is excellent in initial battery capacity and cycle property, and (3) a lithium secondary battery comprising a positive electrode, a negative electrode and a nonaqueous electrolytic solution of an electrolyte salt dissolved in a nonaqueous solvent, wherein the nonaqueous electrolytic solution contains an ester compound having a specific structure in an amount of from 0.01 to 10% by weight of the nonaqueous electrolytic solution.

5 Claims, No Drawings

ESTER COMPOUND, AND NON-AQUEOUS ELECTROLYTE SOLUTION AND LITHIUM SECONDARY BATTERY EACH USING THE ESTER COMPOUND

TECHNICAL FIELD

The present invention relates to an ester compound useful as intermediate materials for medicines, agricultural chemicals, electronic materials, polymer materials and the like, or as battery materials, as well as to a nonaqueous electrolytic solution comprising it, which is excellent in initial battery capacity and cycle property and capable of maintaining battery performance for a long period of time, and also to a lithium secondary battery using it.

BACKGROUND ART

In recent years, lithium secondary batteries have been widely used as driving power supplies for small electronic devices such as mobile telephones, notebook-size personal computers and the like. A lithium secondary batteries are mainly constituted of a positive electrode and a negative electrode containing a material capable of absorbing and releasing lithium, and a nonaqueous electrolytic solution containing a lithium salt, in which a carbonate such as ethylene carbonate (EC), propylene carbonate (PC) and the like are used as the nonaqueous electrolytic solution.

As the negative electrode for the lithium secondary battery, known are metal lithium, and metal compounds (simple metal substances, oxides, alloys with lithium, etc.) and carbon materials capable of absorbing and releasing lithium; and in particular, lithium secondary batteries comprising a carbon material such as coke, artificial graphite, natural graphite and the like capable of absorbing and releasing lithium have been widely put into practical use.

For example, it is known that, in a lithium secondary battery using a highly-crystallized carbon material such as natural graphite, artificial graphite or the like as the negative electrode material therein, the solvent in the nonaqueous electrolytic solution decomposes through reduction on the surface of the negative electrode in charging, and even EC widely used as a solvent for nonaqueous electrolytic solution may partly decompose through reduction during repeated charging and discharging, therefore causing deterioration of battery performance such as battery capacity and cycle property.

Further, it is known that a lithium secondary battery using, as the negative electrode material therein, lithium metal or its alloy, or a simple metal substance such as tin, silicon or the like or its oxide, may have a high initial capacity, in which, however, the negative electrode material may be powdered during cycles and, as compared with a negative electrode of a carbon material, it may accelerate the reductive decomposition of the solvent of the electrolytic solution, therefore greatly deteriorating battery performance such as battery capacity and cycle property.

On the other hand, in a lithium secondary battery comprising, for example, $LiCoO_2$, $LiMn_2O_4$, $LiNiO_2$ or the like as the positive electrode therein, when the solvent in the nonaqueous electrolytic solution has a high temperature in a charged state, then it partly decomposes through oxidation locally in the interface between the positive electrode material and the nonaqueous electrolytic solution, and the decomposed product interferes with the desired electrochemical reaction in the battery, therefore deteriorating battery performance.

As in the above, the decomposition of an electrolytic solution on a positive electrode and a negative electrode brings about gas generation therearound to swell the battery, or brings about gas retention between a positive electrode and a negative electrode to interfere with lithium ion movement, therefore being a cause of deteriorating battery performance. Despite of the situation, electronic appliances equipped with lithium secondary batteries therein are in a stream of further increase in the power consumption and, with that, the capacity of lithium secondary batteries is being much increased, therefore bringing about problems in that the electrolytic solution is being much more easily decomposable and the battery characteristics such as cycle property are more worsened.

Patent Documents 1 and 2 disclose a nonaqueous electrolytic battery in which the nonaqueous electrolytic solution comprises, as dissolved therein, a methoxybenzene-based compound partly substituted with a fluorine atom or the like, proposing a method of evading thermal runaway by redox reaction in an overcharged state. However, these do not refer at all to cycle property, and are therefore not on a satisfactory level.

Patent Document 3 and Patent Document 4 disclose a nonaqueous electrolytic solution with methyl benzoate or vinyl benzoate dissolved therein, proposing a battery effective for the affinity to a carbon material and for the initial charge-discharge efficiency. However, these do not refer at all to cycle property, and are therefore not on a satisfactory level.

Patent Document 5 discloses a method for producing, as a production material for antimicrobial agents, methyl 3-methoxy-2,4,5-trifluorobenzoate from 3-methoxy-2,4,5-trifluorobenzoic acid, using dimethyl sulfate.

Patent Document 6 discloses a lithium secondary battery comprising a nonaqueous electrolytic solution of, as dissolved therein, methyl benzoate partly substituted with a fluorine atom or the like, indicating that the lithium secondary battery has a higher discharging capacity than a lithium secondary battery comprising a nonaqueous electrolytic solution of, as dissolved therein, methyl benzoate not substituted with a fluorine atom or the like. However, even the battery is not still on a satisfactory level in point of the initial battery capacity and the cycle property thereof.

[Patent Document 1] JP-A 10-308236
[Patent Document 2] JP-A 2000-156243
[Patent Document 3] JP-A 8-293323
[Patent Document 4] JP-A 2000-299127
[Patent Document 5] JP-A 3-127755
[Patent Document 6] JP-A 2000-323169

DISCLOSURE OF THE INVENTION

Problems that the Invention is to Solve

An object of the present invention is to provide an ester compound useful as intermediate materials for various materials, or as battery materials, as well as a nonaqueous electrolytic solution for lithium secondary battery using it, which is excellent in initial battery capacity and cycle property and capable of maintaining good battery performance for a long period of time, and also to a lithium secondary battery using it.

Means for Solving the Problems

The present inventors have assiduously studied for the purpose of solving the above-mentioned problems and, as a result, have found that, for a nonaqueous electrolytic solution of an electrolyte salt dissolved in a nonaqueous solvent, when an ester compound having an alkoxy group and a fluorine atom on a benzene ring such as propargyl 3-methoxy-2,4,5-trifluorobenzoate or the like is produced and added to the nonaqueous electrolytic solution, then a lithium secondary battery excellent in the initial battery capacity and the cycle property thereof and capable of maintaining the battery performance for a long period of time can be obtained, and have completed the present invention.

In addition, the present inventors have further found that, for a nonaqueous electrolytic solution of an electrolyte salt dissolved in a nonaqueous solvent, when propargyl 2,4-trifluorobenzoate or the like having a fluorine atom on the benzene ring and having an unsaturated bonding site is added to the nonaqueous electrolytic solution, then a lithium secondary battery excellent in the initial battery capacity and the cycle property thereof can be obtained, and have completed the present invention.

Specifically, the present invention provides the following (1) to (4):

(1) An ester compound represented by the following general formula (I) or (II):

[Formula 1]

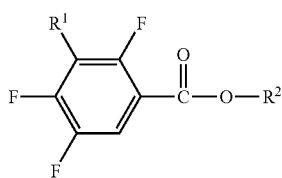

(I)

(wherein $R^1$ represents a methoxy group or an ethoxy group; $R^2$ represents a linear or branched alkenyl group having from 2 to 6 carbon atoms, a linear or branched alkynyl group having from 3 to 6 carbon atoms, a phenyl group or a biphenyl group);

[Formula 2]

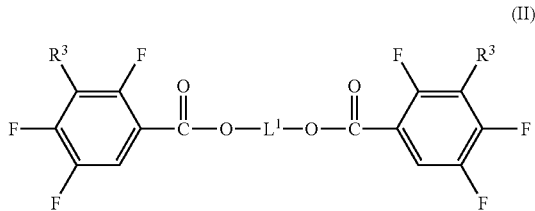

(II)

(wherein $R^3$ represents a methoxy group or an ethoxy group; $L^1$ represents a linear or branched alkylene group having from 2 to 6 carbon atoms, a linear or branched alkenylene group having from 4 to 6 carbon atoms, or a linear or branched alkynylene group having from 4 to 6 carbon atoms).

(2) A nonaqueous electrolytic solution for lithium secondary battery, comprising an electrolyte dissolved in a nonaqueous solvent and containing an ester compound represented by the following general formula (III) in an amount of from 0.01 to 10% by weight of the nonaqueous electrolytic solution:

[Formula 3]

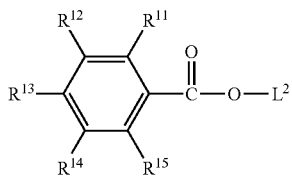

(III)

(wherein $R^{11}$, $R^{13}$, $R^{14}$ and $R^{15}$ each independently represent a hydrogen atom or a fluorine atom; $R^{12}$ represents a hydrogen atom, a fluorine atom, a methoxy group or an ethoxy group; at least one of $R^{11}$ to $R^{15}$ is a fluorine atom; $L^2$ represents an alkyl group having from 1 to 6 carbon atoms, an alkenyl group having from 2 to 6 carbon atoms, an alkynyl group having from 3 to 6 carbon atoms, a phenyl group or a biphenyl group; provided that when all of $R^{11}$ to $R^{15}$ are fluorine atoms, then $L^2$ represents an alkenyl group having from 2 to 6 carbon atoms, an alkynyl group having from 3 to 6 carbon atoms, a phenyl group or a biphenyl group).

(3) A nonaqueous electrolytic solution comprising an electrolyte salt dissolved in a nonaqueous solvent and containing an ester compound represented by the following general formula (II) and/or (IV) in an amount of from 0.01 to 10% by weight of the nonaqueous electrolytic solution:

[Formula 4]

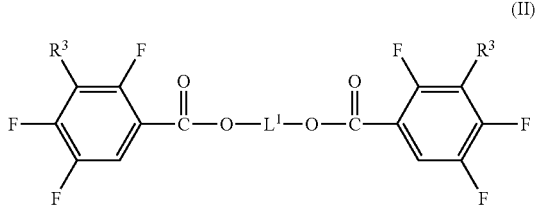

(II)

(wherein $R^3$ and $L^1$ have the same meanings as above),

[Formula 5]

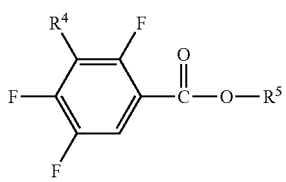

(IV)

(wherein $R^4$ represents a methoxy group or an ethoxy group; $R^5$ represents a linear or branched alkyl group having from 1 to 6 carbon atoms, a linear or branched alkenyl group having from 2 to 6 carbon atoms, a linear or branched alkynyl group having from 3 to 6 carbon atoms, a phenyl group or a biphenyl group).

(4) A lithium secondary battery comprising a positive electrode, a negative electrode and a nonaqueous electrolytic solution of an electrolyte salt dissolved in a nonaqueous solvent, wherein the nonaqueous electrolytic solution contains at least one ester compound selected from those of general formulae (II), (III) and (IV) in an amount of from 0.01 to 10% by weight of the nonaqueous electrolytic solution.

Effect of the Invention

The lithium secondary battery comprising the nonaqueous electrolyte of the present invention is excellent in the initial battery capacity and the cycle property thereof and can maintain the battery performance for a long period of time.

BEST MODE FOR CARRYING OUT THE INVENTION

The ester compound, the nonaqueous electrolytic solution for lithium secondary battery using it, and the lithium secondary battery using it of the present invention are described in detail hereinunder.

The ester compound of the present invention is represented by the following general formulas (I) or (II):

[Ester Compound Represented by General Formula (I)]

[Formula 6]

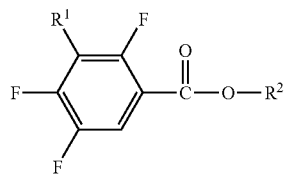

(I)

(wherein $R^1$ represents a methoxy group or an ethoxy group; $R^2$ represents a linear or branched alkenyl group having from 2 to 6 carbon atoms, a linear or branched alkynyl group having from 3 to 6 carbon atoms, a phenyl group or a biphenyl group).

$R^1$ in the general formula (I) is a methoxy group or an ethoxy group, preferably a methoxy group.

The linear or branched alkenyl group having from 2 to 6 carbon atoms for $R^2$ includes a vinyl group, a 2-propenyl group, a 2-butenyl group, a 3-butenyl group, a 4-pentenyl group, a 2-methyl-2-propenyl group, a 2-methyl-2-butenyl group, a 3-methyl-2-butenyl group, etc. The linear or branched alkynyl group having from 3 to 6 carbon atoms for $R^2$ includes a 2-propynyl group, a 2-butynyl group, a 3-butynyl group, a 4-pentynyl group, a 5-hexynyl group, a 1-methyl-2-propynyl group, a 1-methyl-2-butynyl group, a 1,1-dimethyl-2-propynyl group, etc.

The phenyl group for $R^2$ may be substituted with an alkyl group having from 1 to 6 carbon atoms or a fluorine atom, including a phenyl group, a tolyl group, a xylyl group, a mesityl group, a fluorophenyl group, etc. The biphenyl group for $R^2$ may be substituted with an alkyl group having from 1 to 6 carbon atoms or a fluorine atom.

The ester compound represented by the general formula (I) includes, concretely, vinyl 3-methoxy-2,4,5-trifluorobenzoate [$R^1$=methoxy group, $R^2$=vinyl group], 2-propenyl 3-methoxy-2,4,5-trifluorobenzoate [$R^1$=methoxy group, $R^2$=2-propenyl group], 2-butenyl 3-methoxy-2,4,5-trifluorobenzoate [$R^1$=methoxy group, $R^2$=2-butenyl group], 3-butenyl 3-methoxy-2,4,5-trifluorobenzoate [$R^1$=methoxy group, $R^2$=3-butenyl group], 4-pentenyl 3-methoxy-2,4,5-trifluorobenzoate [$R^1$=methoxy group, $R^2$=4-pentenyl group], 2-methyl-2-propenyl 3-methoxy-2,4,5-trifluorobenzoate [$R^1$=methoxy group, $R^2$=2-methyl-2-propenyl group], 3-methyl-2-butenyl 3-methoxy-2,4,5-trifluorobenzoate [$R^1$=methoxy group, $R^2$=3-methyl-2-butenyl group], 2-propynyl 3-methoxy-2,4,5-trifluorobenzoate [$R^1$=methoxy group, $R^2$=2-propynyl group], 2-butynyl 3-methoxy-2,4,5-trifluorobenzoate [$R^1$=methoxy group, $R^2$=2-butynyl group], 4-pentynyl 3-methoxy-2,4,5-trifluorobenzoate [$R^1$=methoxy group, $R^2$=4-pentynyl group], 5-hexynyl 3-methoxy-2,4,5-trifluorobenzoate [$R^1$=methoxy group, $R^2$=5-hexynyl group], 1-methyl-2-propynyl 3-methoxy-2,4,5-trifluorobenzoate [$R^1$=methoxy group, $R^2$=1-methyl-2-propynyl group], 1,1-dimethyl-2-propynyl 3-methoxy-2,4,5-trifluorobenzoate [$R^1$=methoxy group, $R^2$=1,1-dimethyl-2-propynyl group], phenyl 3-methoxy-2,4,5-trifluorobenzoate [$R^1$=methoxy group, $R^2$=phenyl group], tolyl 3-methoxy-2,4,5-trifluorobenzoate [$R^1$=methoxy group, $R^2$=tolyl group], xylyl 3-methoxy-2,4,5-trifluorobenzoate [$R^1$=methoxy group, $R^2$=xylyl group], biphenyl 3-methoxy-2,4,5-trifluorobenzoate [$R^1$=methoxy group, $R^2$=biphenyl group], vinyl 3-ethoxy-2,4,5-trifluorobenzoate [$R^1$=ethoxy group, $R^2$=vinyl group], 2-propenyl 3-ethoxy-2,4,5-trifluorobenzoate [$R^1$=ethoxy group, $R^2$=propenyl group], 2-propynyl 3-ethoxy-2,4,5-trifluorobenzoate [$R^1$=ethoxy group, $R^2$=2-propynyl group], phenyl 3-ethoxy-2,4,5-trifluorobenzoate [$R^1$=ethoxy group, $R^2$=phenyl group], tolyl 3-ethoxy-2,4,5-trifluorobenzoate [$R^1$=ethoxy group, $R^2$=tolyl group], biphenyl 3-ethoxy-2,4,5-trifluorobenzoate [$R^1$=ethoxy group, $R^2$=biphenyl group], etc.

Of those, preferred are methyl 3-methoxy-2,4,5-trifluorobenzoate, ethyl 3-methoxy-2,4,5-trifluorobenzoate, vinyl 3-methoxy-2,4,5-trifluorobenzoate, 2-propenyl 3-methoxy-2,4,5-trifluorobenzoate, 2-propynyl 3-methoxy-2,4,5-trifluorobenzoate, phenyl 3-methoxy-2,4,5-trifluorobenzoate, tolyl 3-methoxy-2,4,5-trifluorobenzoate, and biphenyl 3-methoxy-2,4,5-trifluorobenzoate.

[Ester Compound Represented by General Formula (II)]

[Formula 7]

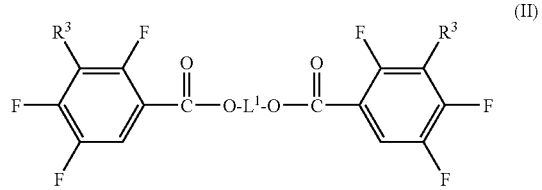

(II)

(wherein $R^3$ represents a methoxy group or an ethoxy group; $L^1$ represents a linear or branched alkylene group having from 2 to 6 carbon atoms, a linear or branched alkenylene group having from 4 to 6 carbon atoms, or a linear or branched alkynylene group having from 4 to 6 carbon atoms).

$R^3$ in the general formula (II) is a methoxy group or an ethoxy group, preferably a methoxy group.

The linear or branched alkylene (alkanediyl) group having from 2 to 6 carbon atoms for $L^1$ includes an ethylene group, a 1,2-propylene group, a 1,3-propylene group, a 1,2-butylene group, a 1,3-butylene group, a 1,4-butylene group, a 2,3-butylene group, a 1,3-pentylene group, a 1,4-pentylene group, a 1,5-pentylene group, a 2,4-pentylene group, a 1,5-hexylene group, a 1,6-hexylene group, a 2,4-hexylene group, etc. Of those, preferred is a branched alkylene group such as a 1,2-propylene group, a 1,3-butylene group, a 2,3-butylene group, a 1,4-pentylene group, a 2,4-pentylene group, a 2,4-hexylene group, etc.; and more preferred is an alkylene group branched with a methyl group, such as 1,2-propylene group (propan-1-2-diyl group), a 1,3-butylene group, a 2,3-butylene group, etc.

The linear or branched alkenylene group having from 4 to 6 carbon atoms for $L^1$ includes a 2-butenylene group, a 2-pentenylene group, 2-hexenylene, a 3-hexenylene group, a 1,4-dimethyl-2-butenylene group, etc.

The linear or branched alkynylene group having from 4 to 6 carbon atoms for $L^1$ includes a 2-butynylene group, a 2-pentynylene group, 2-hexynylene, a 3-hexynylene group, a 1,4-dimethyl-2-butynylene group, etc.

The phenyl group and the biphenyl group for $L^1$ may be substituted with an alkyl group having from 1 to 6 carbon atoms or a fluorine atom.

The ester compound represented by the general formula (II) includes, concretely, ethylene glycol bis(3-methoxy-2,4,5-trifluorobenzoate) [$R^3$=methoxy group, $L^1$=ethylene group], 1,2-propanediol bis(3-methoxy-2,4,5-trifluorobenzoate) [$R^3$=methoxy group, $L^1$=1,2-propylene group], 1,3-propanediol bis(3-methoxy-2,4,5-trifluorobenzoate) [$R^3$=methoxy group, $L^1$=1,3-propylene group], 1,3-butanediol bis(3-methoxy-2,4,5-trifluorobenzoate) [$R^3$=methoxy group, $L^1$=1,3-butylene group], 1,4-butanediol bis(3-methoxy-2,4,5-trifluorobenzoate) [$R^3$=methoxy group, $L^1$=1,4-butylene group], 2,3-butanediol bis(3-methoxy-2,4,5-trifluorobenzoate) [$R^3$=methoxy group, $L^1$=2,3-butylene group], 1,3-dimethyl-1,3-propanediol bis(3-methoxy-2,4,5-trifluorobenzoate) [$R^3$=methoxy group, $L^1$=2,4-pentylene group], 1,4-dimethyl-1,4-butanediol bis(3-methoxy-2,4,5-trifluorobenzoate) [$R^3$=methoxy group, $L^1$=2,5-hexylene group], 2-butene-1,4-diol bis(3-methoxy-2,4,5-trifluorobenzoate) [$R^3$=methoxy group, $L^1$=2-butenylene group], 2-butyne-1,4-diol bis(3-methoxy-2,4,5-trifluorobenzoate) [$R^3$=methoxy group, $L^1$=2-butynylene group], etc.

Of those, preferred are ethylene glycol bis(3-methoxy-2,4,5-trifluorobenzoate), 1,2-propanediol bis(3-methoxy-2,4,5-trifluorobenzoate), 1,3-propanediol bis(3-methoxy-2,4,5-trifluorobenzoate), 1,2-butanediol bis(3-methoxy-2,4,5-trifluorobenzoate), 1,3-butanediol bis(3-methoxy-2,4,5-trifluorobenzoate), 1,4-butanediol bis(3-methoxy-2,4,5-trifluorobenzoate), 2,3-butanediol bis(3-methoxy-2,4,5-trifluorobenzoate), 2-butyne-1,4-diol bis(3-methoxy-2,4,5-trifluorobenzoate); and more preferred are compounds having an alkylene group branched with a methyl group such as 1,2-propanediol bis(3-methoxy-2,4,5-trifluorobenzoate), 1,3-butanediol bis(3-methoxy-2,4,5-trifluorobenzoate), 2,3-butanediol bis(3-methoxy-2,4,5-trifluorobenzoate), etc.

[Production Method for Ester Compound Represented by General Formula (I)]

The ester compound represented by the general formula (I) of the present invention can be produced according to (a) a transesterification method and (b) an acid chloride method mentioned below; however, the present invention is not limited to these production methods.

(a) Transesterification Method:

The transesterification method is a method for producing the intended ester compound through transesterification of 3-methoxy-2,4,5-trifluorobenzoic acid (hereinafter referred to as "MTFBA") in a solvent or not in a solvent, in the presence of a base and a metal catalyst.

The ester compound to be transesterified with MTFBA includes a fatty acid ester, for example, an acetate such as vinyl acetate, as well as a propionate, a butyrate, a valerate, etc. Of those, more preferred is an acetate. The amount of the ester to be used is preferably from 1 to 50 mols, more preferably from 4 to 20 mols, relative to 1 mol of MTFBA.

The metal catalyst to be used in the transesterification includes a divalent palladium compound, a divalent iridium compound, etc. Concretely, preferred are Pd(OAc)$_2$, Pd(OCOEt)$_2$, PdCl$_2$, Li$_2$PdCl$_4$, [Ir(cod)Cl]$_2$, and mixtures of those compounds, etc.

The amount of the metal catalyst to be used is preferably from 0.001 to 20% by weight of the overall weight of the reaction liquid, more preferably from 0.01 to 10% by weight, even more preferably from 0.1 to 5% by weight.

The base catalyst includes an alkali metal or alkaline earth metal hydroxide, carbonate, phosphate, acetate and their mixtures, etc. Concretely, preferred are potassium hydroxide, potassium carbonate, sodium hydroxide, sodium carbonate, sodium hydrogencarbonate, sodium acetate, lithium hydroxide. The amount of the base catalyst to be used is preferably from 0.01 to 20% by weight of the overall weight of the reaction liquid, more preferably from 0.05 to 10% by weight, even more preferably from 0.1 to 5% by weight.

In the transesterification, usable is a solvent inert under the reaction condition. The usable inert solvent includes aliphatic hydrocarbons such as hexane, heptane, etc.; halogenohydrocarbons such as dichloroethane, dichloropropane, etc.; aromatic hydrocarbons such as toluene, xylene, etc.; halogenoaromatic hydrocarbons such as chlorobenzene, fluorobenzene, etc.; ethers such as diethyl ether, etc.; nitriles such as acetonitrile, propionitrile, etc.; amides such as N,N-dimethylformamide, etc.; sulfoxides such as dimethyl sulfoxide, etc.; nitro compounds such as nitromethane, nitroethane, etc.; or their mixtures. Especially preferred are toluene, xylene, N,N-dimethylformamide. The amount of the inert solvent to be used is preferably from 0.01 to 20 parts by weight, more preferably from 1 to 5 parts by weight, relative to 1 part by weight of MTFBA.

The temperature in the transesterification is preferably not lower than −20° C., more preferably not lower than 0° C. so as not to lower the reactivity. The uppermost limit of the reaction temperature is preferably 80° C. or lower, more preferably 60° C. or lower. When the reaction temperature exceeds 80° C., then side reaction or decomposition of products may occur.

The reaction time varies depending on the reaction temperature and the scale, but is preferably from 0.5 to 30 hours, more preferably from 1 to 48 hours. When the reaction time is too short, then the unreacted matter may remain; but on the contrary, when the reaction time is too long, then the product may be decomposed or side reaction may occur.

(b) Acid Chloride Method:

The acid chloride method is a method for producing the intended ester compound through esterification of an acid chloride of MTFBA with an alcohol in a solvent or not in a solvent in the presence of a base.

The amount of the alcohol to be reacted with an acid chloride of MTFBA is preferably from 1 to 20 mols relative to 1 mol of MTFBA, more preferably from 1 to 5 mols. The acid chloride of MTFBA can be prepared through reaction of MTFBA with thionyl chloride.

In producing the ester compound from the acid chloride, hydrogen chloride gas is produced as a by product. Not collected, the hydrogen chloride gas may be removed away from the reaction system and absorbed by a neutralization tank; or a base is made to exist in the reaction system, and the gas may be caught through neutralization in the reaction system. For removing the hydrogen chloride gas away from the reaction system, there may be employed a method of bubbling the reaction liquid with an inert gas; or a method of exposing the reaction liquid to a reduced pressure. In any case, the range of the operation temperature is preferably from 0 to 100° C.

In case where the ester is produced from an acid chloride of MTFBA not using a base, a solvent may be used or may not be used. In case where the ester is produced using a base, it is desirable to additionally use a solvent inert under the reaction condition, as a neutralized salt exists in the reaction system.

The inert solvent usable in common in any case includes aliphatic hydrocarbons such as hexane, heptane, etc.; halogenohydrocarbons such as dichloroethane, dichloropropane, etc.; aromatic hydrocarbons such as toluene, xylene, etc.; halogenoaromatic hydrocarbons such as chlorobenzene, fluorobenzene, etc.; ethers such as diethyl ether, etc.; nitriles such as acetonitrile, propionitrile, etc.; amides such as N,N-dimethylformamide, etc.; sulfoxides such as dimethyl sulfoxide, etc.; nitro compounds such as nitromethane, nitroethane, etc.; or their mixtures. Especially preferred are toluene, xylene, N,N-dimethylformamide. The amount of the inert solvent to be used is preferably from 0 to 10 parts by weight, more preferably from 1 to 2 parts by weight, relative to 1 part by weight of MTFBA.

As the base, usable are any of an inorganic base and an organic base. These may be used singly or as combined. The inorganic base usable herein includes potassium carbonate, sodium carbonate, calcium hydroxide, calcium oxide, etc. The organic base usable herein includes linear-chain or branched-chain aliphatic tertiary amines, and mono-substituted or poly-substituted pyrrole, pyrrolidone, imidazole, imidazolidinone, pyridine, pyrimidine, quinoline, N,N-dialkylcarboxyamide, etc.

Of those, especially preferred are trialkylamines such as trimethylamine, triethylamine, tripropylamine, tributylamine, ethyldiisopropylamine, etc.; and pyridine, N-methylpyrrolidone, N,N-dimethylacetamide, N,N-dimethylaminopyridine, 1,3-dimethylimidazolidinone. The amount of the base to be used is preferably from 0.8 to 5 mols relative to 1 mol of MTFBA, more preferably from 1 to 3 mols, even more preferably from 1 to 1.5 mols, as capable of preventing production of side products.

In the reaction of an acid chloride of MTFBA with an alcohol, the lowermost limit of the reaction temperature is preferably −20° C. or higher, more preferably 0° C. or higher so as not to lower the reactivity. The uppermost limit of the reaction temperature is preferably 80° C. or lower, more preferably 60° C. or lower. When the reaction temperature exceeds 80° C., then side reaction or decomposition of products may occur.

The reaction time varies depending on the reaction temperature and the scale, but is preferably from 0.1 to 12 hours, more preferably from 0.2 to 6 hours. When the reaction time is too short, then the unreacted matter may remain; but on the contrary, when the reaction time is too long, then the product may be decomposed or side reaction may occur.

[Production Method for Ester Compound Represented by General Formula (II)]

The ester compound represented by the general formula (II) of the present invention can be produced according to the above-mentioned acid chloride method (b). Specifically, the compound may be produced through esterification of an acid chloride of MTFBA with a diol in a solvent or not in a solvent in the presence of a base; however, the production method is not limitative.

The amount of the diol to be reacted with an acid chloride of MTFBA is preferably from 1 to 20 mols, more preferably from 1 to 5 mols, relative to 1 mol of MTFBA.

The type and the amount of the inert solvent and the base to be used are the same as those mentioned in the above; and the reaction temperature and the reaction time are also the same as above.

[Compound Represented by General Formula (III)]

The compound to be in the nonaqueous electrolytic solution in the present invention is represented by the following general formula (III):

[Formula 8]

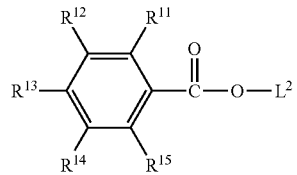

(III)

(wherein $R^{11}$, $R^{13}$, $R^{14}$ and $R^{15}$ each independently represent a hydrogen atom or a fluorine atom; $R^{12}$ represents a hydrogen atom, a fluorine atom, a methoxy group or an ethoxy group; at least one of $R^{11}$ to $R^{15}$ is a fluorine atom; $L^2$ represents an alkyl group having from 1 to 6 carbon atoms, an alkenyl group having from 2 to 6 carbon atoms, an alkynyl group having from 3 to 6 carbon atoms, a phenyl group or a biphenyl group; provided that when all of $R^{11}$ to $R^{15}$ are fluorine atoms, then $L^2$ represents an alkenyl group having from 2 to 6 carbon atoms, an alkynyl group having from 3 to 6 carbon atoms, a phenyl group or a biphenyl group).

The alkenyl group having from 2 to 6 carbon atoms for $L^2$ includes a linear alkenyl group such as an ethenyl group (vinyl group), a 2-propenyl group (allyl group), a 2-butenyl group, a 3-butenyl group, a 4-pentenyl group, etc.; and a branched alkenyl group such as a 2-methyl-2-propenyl group, a 3-methyl-2-butenyl group, etc.

The alkynyl group having from 3 to 6 carbon atoms for $L^2$ includes a linear alkynyl group such as 2-propynyl group (propargyl group), a 2-butynyl group, a 3-butynyl group, a 4-pentynyl group, a 5-hexynyl group, etc.; and a branched alkynyl group such as a 1-methyl-2-propynyl group, a 1-methyl-2-butynyl group, a 1,1-dimethyl-2-propynyl group, etc.

The phenyl group for $L^2$ may be substituted with an alkyl group having from 1 to 6 carbon atoms or a fluorine atom, including a phenyl group, a tolyl group, a xylyl group, a mesityl group, a fluorophenyl group, etc. The biphenyl group may be substituted with an alkyl group having from 1 to 6 carbon atoms or a fluorine atom.

Of the ester compounds represented by the general formula (III), linear alkenyl esters include, concretely, vinyl 2-fluorobenzoate [$R^{11}$=fluorine atom, $R^{12}$=$R^{13}$=$R^{14}$=$R^{15}$=hydrogen atom, $L^2$=vinyl group], vinyl 3-fluorobenzoate [$R^{12}$=fluorine atom, $R^{11}$=$R^{13}$=$R^{14}$=$R^{15}$=hydrogen atom, $L^2$=vinyl group], vinyl 4-fluorobenzoate [$R^{13}$=fluorine atom, $R^{11}$=$R^{12}$=$R^{14}$=$R^{15}$=hydrogen atom, $L^2$=vinyl group], vinyl 2,4-difluorobenzoate [$R^{11}$=$R^{13}$=fluorine atom, $R^{12}$=$R^{14}$=$R^{15}$=hydrogen atom, $L^2$=vinyl group], vinyl 2,6-difluorobenzoate [$R^{11}$=$R^{15}$=fluorine atom, $R^{12}$=$R^3$=$R^{14}$=hydrogen atom, $L^2$=vinyl group], vinyl 2,4,6-trifluorobenzoate [$R^{11}$=$R^{13}$=$R^{15}$=fluorine atom, $R^{12}$=$R^{14}$=hydrogen atom, $L^2$=vinyl group], vinyl 2,3,4,6-tetrafluorobenzoate [$R^{11}$=$R^{12}$=$R^{13}$=$R^{15}$=fluorine atom, $R^{14}$=hydrogen atom, $L^2$=vinyl group], vinyl 2,3,4,5,6-pentafluorobenzoate [$R^{11}$=$R^{12}$=$R^{13}$=$R^{14}$=$R^{15}$=fluorine atom, $L^2$=vinyl group], 2-propenyl 2-fluorobenzoate [$R^{11}$=fluorine atom, $R^{12}$=$R^{13}$=$R^{14}$=$R^{15}$=hydrogen atom, $L^2$=2-propenyl group], 2-propenyl 3-fluorobenzoate [$R^{12}$=fluorine atom, $R^{11}$=$R^{13}$=$R^{14}$=$R^{15}$=hydrogen atom, $L^2$=2-propenyl group], 2-propenyl 4-fluorobenzoate [$R^{13}$=fluorine atom, $R^{11}$=$R^{12}$=$R^{14}$=$R^{15}$=hydrogen atom, $L^2$=2-propenyl group], 2-propenyl 2,4-difluorobenzoate [$R^{11}$=$R^{13}$=fluorine atom, $R^{12}$=$R^{14}$=$R^{15}$=hydrogen atom, $L^2$=2-propenyl group], 2-propenyl 2,6-difluorobenzoate

[$R^{11}$=$R^{15}$=fluorine atom, $R^{12}$=$R^{13}$=$R^{14}$=hydrogen atom, $L^2$=2-propenyl group], 2-propenyl 2,4,6-trifluorobenzoate [$R^{11}$=$R^{13}$=$R^{15}$=fluorine atom, $R^{12}$=$R^{14}$=hydrogen atom, $L^2$=2-propenyl group], 2-propenyl 2,3,4,6-tetrafluorobenzoate [$R^{11}$=$R^{12}$=$R^{13}$=$R^{15}$=fluorine atom, $R^{14}$=hydrogen atom, $L^2$=2-propenyl group], 2-propenyl 2,3,4,5,6-pentafluorobenzoate [$R^{11}$=$R^{12}$=$R^{13}$=$R^{14}$=$R^{15}$=fluorine atom, $L^2$=2-propenyl group], 2-butenyl 2-fluorobenzoate [$R^{11}$=fluorine atom, $R^{12}$=$R^{13}$=$R^{14}$=$R^{15}$=hydrogen atom, $L^2$=2-butenyl group], 2-butenyl 3-fluorobenzoate [$R^{12}$=fluorine atom, $R^{11}$=$R^{13}$=$R^{14}$=$R^{15}$=hydrogen atom, $L^2$=2-butenyl group], 2-butenyl 4-fluorobenzoate [$R^{13}$=fluorine atom, $R^{11}$=$R^{12}$=$R^{14}$=$R^{15}$=hydrogen atom, $L^2$=2-butenyl group], 2-butenyl 2,4-difluorobenzoate [$R^{11}$=$R^{13}$=fluorine atom, $R^{12}$=$R^{14}$=$R^{15}$=hydrogen atom, $L^2$=2-butenyl group], 2-butenyl 2,6-difluorobenzoate [$R^{11}$=$R^{15}$=fluorine atom, $R^{12}$=$R^{13}$=$R^{14}$=hydrogen atom, $L^2$=2-butenyl group], 2-butenyl 2,4,6-trifluorobenzoate [$R^{11}$=$R^{13}$=$R^{15}$=fluorine atom, $R^{12}$=$R^{14}$=hydrogen atom, $L^2$=2-butenyl group], 2-butenyl 2,3,4,6-tetrafluorobenzoate [$R^{11}$=$R^{12}$=$R^{13}$=$R^{15}$=fluorine atom, $R^{14}$=hydrogen atom, $L^2$=2-butenyl group], 2-butenyl 2,3,4,5,6-pentafluorobenzoate [$R^{11}$=$R^{12}$=$R^{13}$=$R^{14}$=$R^{15}$=fluorine atom, $L^2$=2-butenyl group], 3-butenyl 2-fluorobenzoate [$R^{11}$=fluorine atom, $R^{12}$=$R^{13}$=$R^{14}$=$R^{15}$=hydrogen atom, $L^2$=3-butenyl group], 3-butenyl 3-fluorobenzoate [$R^{12}$=fluorine atom, $R^{11}$=$R^{13}$=$R^{14}$=$R^{15}$=hydrogen atom, $L^2$=3-butenyl group], 3-butenyl 4-fluorobenzoate [$R^{13}$=fluorine atom, $R^{11}$=$R^{12}$=$R^{14}$=$R^{15}$=hydrogen atom, $L^2$=3-butenyl group], 3-butenyl 2,4-difluorobenzoate [$R^{11}$=$R^{13}$=fluorine atom, $R^{12}$=$R^{14}$=$R^{15}$=hydrogen atom, $L^2$=3-butenyl group], 3-butenyl 2,6-difluorobenzoate [$R^{11}$=$R^{15}$=fluorine atom, $R^{12}$=$R^{13}$=$R^{14}$=hydrogen atom, $L^2$=3-butenyl group], 3-butenyl 2,4,6-trifluorobenzoate [$R^{11}$=$R^{13}$=$R^{15}$=fluorine atom, $R^{12}$=$R^{14}$=hydrogen atom, $L^2$=3-butenyl group], 3-butenyl 2,3,4,6-tetrafluorobenzoate [$R^{11}$=$R^{12}$=$R^{13}$=$R^{15}$=fluorine atom, $R^{14}$=hydrogen atom, $L^2$=3-butenyl group], 3-butenyl 2,3,4,5,6-pentafluorobenzoate [$R^{11}$=$R^{12}$=$R^{13}$=$R^{14}$=$R^{15}$=fluorine atom, $L^2$=3-butenyl group], 4-pentenyl 2-fluorobenzoate [$R^{11}$=fluorine atom, $R^{12}$=$R^{13}$=$R^{14}$=$R^{15}$=hydrogen atom, $L^2$=4-pentenyl group], 4-pentenyl 3-fluorobenzoate [$R^{12}$=fluorine atom, $R^{11}$=$R^{13}$=$R^{4}$=$R^{15}$=hydrogen atom, $L^2$=4-pentenyl group], 4-pentenyl 4-fluorobenzoate [$R^{13}$=fluorine atom, $R^{11}$=$R^{12}$=$R^{14}$=$R^{15}$=hydrogen atom, $L^2$=4-pentenyl group], 4-pentenyl 2,4-difluorobenzoate [$R^{11}$=$R^{13}$=fluorine atom, $R^{12}$=$R^{14}$=$R^{15}$=hydrogen atom, $L^2$=4-pentenyl group], 4-pentenyl 2,6-difluorobenzoate [$R^{11}$=$R^{15}$=fluorine atom, $R^{12}$=$R^{13}$=$R^{14}$=hydrogen atom, $L^2$=4-pentenyl group], 4-pentenyl 2,4,6-trifluorobenzoate [$R^{11}$=$R^{13}$=$R^{15}$=fluorine atom, $R^{12}$=$R^{14}$=hydrogen atom, $L^2$=4-pentenyl group], 4-pentenyl 2,3,4,6-tetrafluorobenzoate [$R^{11}$=$R^{12}$=$R^{13}$=$R^{15}$=fluorine atom, $R^{14}$=hydrogen atom, $L^2$=4-pentenyl group], 4-pentenyl 2,3,4,5,6-pentafluorobenzoate [$R^{11}$=$R^{12}$=$R^{13}$=$R^{14}$=$R^{15}$=fluorine atom, $L^2$=4-pentenyl group], etc.

Branched alkenyl esters include 2-methyl-2-propenyl 2-fluorobenzoate [$R^1$=fluorine atom, $R^{12}$=$R^{13}$=$R^{14}$=$R^{15}$=hydrogen atom, $L^2$=2-methyl-2-propenyl group], 2-methyl-2-propenyl 3-fluorobenzoate [$R^{12}$=fluorine atom, $R^{11}$=$R^{13}$=$R^{14}$=$R^{15}$=hydrogen atom, $L^2$=2-methyl-2-propenyl group], 2-methyl-2-propenyl 4-fluorobenzoate [$R^{13}$=fluorine atom, $R^{11}$=$R^{12}$=$R^{14}$=$R^{15}$=hydrogen atom, $L^2$=2-methyl-2-propenyl group], 2-methyl-2-propenyl 2,4-difluorobenzoate [$R^{11}$=$R^{13}$=fluorine atom, $R^{12}$=$R^{14}$=$R^{15}$=hydrogen atom, $L^2$=2-methyl-2-propenyl group], 2-methyl-2-propenyl 2,6-difluorobenzoate [$R^{11}$=$R^{15}$=fluorine atom, $R^{12}$=$R^{13}$=$R^{14}$=hydrogen atom, $L^2$=2-methyl-2-propenyl group], 2-methyl-2-propenyl 2,4,6-trifluorobenzoate [$R^{11}$=$R^{13}$=$R^{15}$=fluorine atom, $R^{12}$=$R^{14}$=hydrogen atom, $L^2$=2-methyl-2-propenyl group], 2-methyl-2-propenyl 2,3,4,6-tetrafluorobenzoate [$R^{11}$=$R^{12}$$R^{13}$=$R^{15}$=fluorine atom, $R^{14}$=hydrogen atom, $L^2$=2-methyl-2-propenyl group], 2-methyl-2-propenyl 2,3,4,5,6-pentafluorobenzoate [$R^{11}$=$R^{12}$=$R^{13}$=$R^{14}$=$R^{15}$=fluorine atom, $L^2$=2-methyl-2-propenyl group], 3-methyl-2-butenyl 2-fluorobenzoate [$R^{11}$=fluorine atom, $R^{12}$=$R^{13}$=$R^{14}$=$R^{15}$=hydrogen atom, $L^2$=3-methyl-2-butenyl group], 3-methyl-2-butenyl 3-fluorobenzoate [$R^{12}$=fluorine atom, $R^{11}$=$R^{13}$=$R^{14}$=$R^{15}$=hydrogen atom, $L^2$=3-methyl-2-butenyl group], 3-methyl-2-butenyl 4-fluorobenzoate [$R^{13}$=fluorine atom, $R^{11}$=$R^{12}$=$R^{14}$=$R^{15}$=hydrogen atom, $L^2$=3-methyl-2-butenyl group], 3-methyl-2-butenyl 2,4-difluorobenzoate [$R^{11}$=$R^{13}$=fluorine atom, $R^{12}$=$R^{14}$=$R^{15}$=hydrogen atom, $L^2$=3-methyl-2-butenyl group], 3-methyl-2-butenyl 2,6-difluorobenzoate [$R^{11}$=$R^{15}$=fluorine atom, $R^{12}$=$R^{13}$=$R^{14}$=hydrogen atom, $L^2$=3-methyl-2-butenyl group], 3-methyl-2-butenyl 2,4,6-trifluorobenzoate [$R^{11}$=$R^{13}$=$R^{15}$=fluorine atom, $R^{12}$=$R^{14}$=hydrogen atom, $L^2$=3-methyl-2-butenyl group], 3-methyl-2-butenyl 2,3,4,6-tetrafluorobenzoate [$R^{11}$=$R^{12}$=$R^{3}$=$R^{15}$=fluorine atom, $R^{14}$=hydrogen atom, $L^2$=3-methyl-2-butenyl group], 3-methyl-2-butenyl 2,3,4,5,6-pentafluorobenzoate [$R^1$=$R^{12}$=$R^{13}$=$R^{14}$=$R^{15}$=fluorine atom, $L^2$=3-methyl-2-butenyl group], etc.

Linear alkynyl esters include 2-propynyl 2-fluorobenzoate [$R^{11}$=fluorine atom, $R^{12}$=$R^{13}$=$R^{14}$=$R^{15}$=hydrogen atom, $L^2$=2-propynyl group], 2-propynyl 3-fluorobenzoate [$R^{12}$=fluorine atom, $R^{11}$=$R^{13}$=$R^{14}$=$R^{15}$=hydrogen atom, $L^2$=2-propynyl group], 2-propynyl 4-fluorobenzoate [$R^{13}$=fluorine atom, $R^{11}$=$R^{12}$=$R^{14}$=$R^{15}$=hydrogen atom, $L^2$=2-propynyl group], 2-propynyl 2,4-difluorobenzoate [$R^{11}$=$R^{13}$=fluorine atom, $R^{12}$=$R^{14}$=$R^{15}$=hydrogen atom, $L^2$=2-propynyl group], 2-propynyl 2,6-difluorobenzoate [$R^{11}$=$R^{15}$=fluorine atom, $R^{12}$=$R^{13}$=$R^{14}$=hydrogen atom, $L^2$=2-propynyl group], 2-propynyl 2,4,6-trifluorobenzoate [$R^{11}$=$R^{13}$=$R^{15}$=fluorine atom, $R^{12}$=$R^{14}$=hydrogen atom, $L^2$=2-propynyl group], 2-propynyl 2,3,4,6-tetrafluorobenzoate [$R^{11}$=$R^{12}$=$R^{13}$=$R^{15}$=fluorine atom, $R^{14}$=hydrogen atom, $L^2$=2-propynyl group], 2-propynyl 2,3,4,5,6-pentafluorobenzoate [$R^{11}$=$R^{12}$=$R^{3}$=$R^{14}$=$R^{15}$=fluorine atom, $L^2$=2-propynyl group], 2-butynyl 2-fluorobenzoate [$R^{11}$=fluorine atom, $R^{12}$=$R^{13}$=$R^{14}$=$R^{15}$=hydrogen atom, $L^2$=2-butynyl group], 2-butynyl 3-fluorobenzoate [$R^{12}$=fluorine atom, $R^{11}$=$R^{13}$=$R^{14}$=$R^{15}$=hydrogen atom, $L^2$=2-butynyl group], 2-butynyl 4-fluorobenzoate [$R^{13}$=fluorine atom, $R^{11}$=$R^{12}$=$R^{14}$=$R^{15}$=hydrogen atom, $L^2$=2-butynyl group], 2-butynyl 2,4-difluorobenzoate [$R^{11}$=$R^{13}$=fluorine atom, $R^{12}$=$R^{14}$=$R^{15}$=hydrogen atom, $L^2$=2-butynyl group], 2-butynyl 2,6-difluorobenzoate [$R^{11}$=$R^{15}$=fluorine atom, $R^2$=$R^{13}$=$R^1$=hydrogen atom, $L^2$=2-butynyl group], 2-butynyl 2,4,6-trifluorobenzoate [$R^{11}$=$R^{13}$=$R^{15}$=fluorine atom, $R^{12}$=$R^{14}$=hydrogen atom, $L^2$=2-butynyl group], 2-butynyl 2,3,4,6-tetrafluorobenzoate [$R^{11}$=$R^{12}$=$R^{13}$=$R^{15}$=fluorine atom, $R^{14}$=hydrogen atom, $L^2$=2-butynyl group], 2-butynyl 2,3,4,5,6-pentafluorobenzoate [$R^{11}$=$R^{12}$=$R^{13}$=$R^{14}$=$R^{15}$=fluorine atom, $L^2$=2-butynyl group], 3-butynyl 2-fluorobenzoate [$R^{11}$=fluorine atom, $R^{12}$=$R^{13}$=$R^{14}$=$R^{15}$=hydrogen atom, $L^2$=3-butynyl group], 3-butynyl 3-fluorobenzoate [$R^{12}$=fluorine atom, $R^{11}$=$R^{13}$=$R^{14}$=$R^{15}$=hydrogen atom, $L^2$=3-butynyl group], 3-butynyl 4-fluorobenzoate [$R^{13}$=fluorine atom, $R^{11}$=$R^{12}$=$R^{14}$=$R^1$=hydrogen atom, $L^2$=3-butynyl group], 3-butynyl 2,4-difluorobenzoate [$R^{11}$=$R^{13}$=fluorine atom, $R^{12}$=$R^{14}$=$R^{15}$=hydrogen atom, $L^2$=3-butynyl group], 3-butynyl 2,6-difluorobenzoate [$R^{11}$=$R^{15}$=fluorine atom, $R^{12}$=$R^{13}$=$R^{14}$=hydrogen atom, $L^2$=3-butynyl group], 3-butynyl 2,4,6-trifluorobenzoate [$R^{11}$=$R^{13}$=$R^{15}$=fluorine atom, $R^{12}$=$R^{14}$=hydrogen atom, $L^2$=3-butynyl group], 3-butynyl 2,3,4,6-tetrafluorobenzoate [$R^{11}$=$R^{12}$=$R^{13}$=$R^{15}$=fluorine atom, $R^{14}$=hydrogen atom, $L^2$=3-butynyl group], 3-butynyl 2,3,4,5,6-pentafluorobenzoate [$R^{11}$=$R^{12}$=$R^{13}$=$R^{14}$=$R^{15}$=fluorine atom, $L^2$=3-butynyl group], 4-pentynyl 2-fluorobenzoate [$R^1$=fluorine atom, $R^{12}$=$R^{13}$=$R^{14}$=$R^{15}$=hydrogen atom, $L^2$=4-pentynyl group], 4-pentynyl 3-fluorobenzoate [$R^{12}$=fluorine atom, $R^{11}$=$R^{13}$=$R^{14}$=$R^{15}$=hydrogen atom, $L^2$=4-pentynyl group], 4-pentynyl 4-fluorobenzoate [$R^{13}$=fluorine atom, $R^{11}$=$R^{12}$=$R^{14}$=$R^{15}$=hydrogen atom, $L^2$=4-pentynyl group], 4-pentynyl 2,4-difluorobenzoate [$R^{11}$=$R^{13}$=fluorine atom, $R^{12}$=$R^{14}$=$R^{15}$=hydrogen atom, $L^2$=4-pentynyl group], 4-pentynyl 2,6-difluorobenzoate [$R^{11}$=$R^{15}$=fluorine atom, $R^{12}$=$R^{13}$=$R^{14}$=hydrogen atom, $L^2$=4-pentynyl group], 4-pentynyl 2,4,6-trifluorobenzoate [$R^{11}$=$R^{13}$=$R^{15}$=fluorine atom, $R^{12}$=$R^{14}$=hydrogen atom, $L^2$=4-pentynyl group], 4-pentynyl 2,3,4,6-tetrafluorobenzoate [$R^{11}$=$R^{12}$=$R^{13}$=$R^{15}$=fluorine atom, $R^{14}$=hydrogen atom, $L^2$=4-pentynyl group], 4-pentynyl 2,3,4,5,6-pentafluorobenzoate [$R^{11}$=$R^{12}$=$R^{13}$=$R^{14}$=$R^{15}$=fluorine atom, $L^2$=4-pentynyl group], 5-hexynyl 2-fluorobenzoate [$R^{11}$ fluorine atom, $R^{12}$=$R^{13}$=$R^{14}$=$R^{15}$=hydrogen atom, $L^2$=5-hexynyl group], 5-hexynyl 3-fluorobenzoate [$R^{12}$=fluorine atom, $R^{11}$=$R^{13}$=$R^{14}$=$R^{15}$=hydrogen atom, $L^2$=5-hexynyl group], 5-hexynyl 4-fluorobenzoate [$R^{13}$=fluorine atom, $R^{11}$=$R^{12}$=$R^{14}$=$R^{15}$=hydrogen atom, $L^2$=5-hexynyl group], 5-hexynyl 2,4-difluorobenzoate [$R^{11}$=$R^{13}$=fluorine atom, $R^{12}$=$R^{14}$=$R^{15}$=hydrogen atom, $L^2$=5-hexynyl group], 5-hexynyl 2,6-difluorobenzoate [$R^{11}$=$R^{15}$=fluorine atom, $R^{12}$=$R^{13}$=$R^{14}$=hydrogen atom, $L^2$=5-hexynyl group], 5-hexynyl 2,4,6-trifluorobenzoate [$R^{11}$=$R^{13}$=$R^{15}$=fluorine atom, $R^{12}$=$R^{14}$=hydrogen atom, $L^2$=5-hexynyl group], 5-hexynyl 2,3,4,6-tetrafluorobenzoate [$R^{11}$=$R^{12}$=$R^{13}$=$R^{15}$=fluorine atom, $R^{14}$=hydrogen atom, $L^2$=5-hexynyl group], 5-hexynyl 2,3,4,5,6-pentafluorobenzoate [$R^{11}$=$R^{12}$=$R^{13}$=$R^{14}$=$R^{15}$=fluorine atom, $L^2$=5-hexynyl group], etc.

Branched-chain alkynyl esters include 1-methyl-2-propynyl 2-fluorobenzoate [$R^{11}$=fluorine atom, $R^{12}$=$R^{13}$=$R^{14}$=$R^{15}$=hydrogen atom, $L^2$=1-methyl-2-propynyl group], 1-methyl-2-propynyl 3-fluorobenzoate [$R^{12}$=fluorine atom, $R^{11}$=$R^{13}$=$R^{14}$=$R^{15}$=hydrogen atom, $L^2$=1-methyl-2-propynyl group], 1-methyl-2-propynyl 4-fluorobenzoate [$R^{13}$=fluorine atom, $R^{11}$=$R^{12}$=$R^{14}$=$R^{15}$=hydrogen atom, $L^2$=1-methyl-2-propynyl group], 1-methyl-2-propynyl 2,4-difluorobenzoate [$R^{11}$=$R^{13}$=fluorine atom, $R^{12}$=$R^{14}$=$R^{15}$=hydrogen atom, $L^2$=1-methyl-2-propynyl group], 1-methyl-2-propynyl 2,6-difluorobenzoate [$R^{11}$=$R^5$=fluorine atom, $R^2$=$R^{13}$=$R^1$=hydrogen atom, $L^2$=1-methyl-2-propynyl group], 1-methyl-2-propynyl 2,4,6-trifluorobenzoate [$R^{11}$=$R^{13}$=$R^{15}$=fluorine atom, $R^{12}$=$R^{14}$=hydrogen atom, $L^2$=1-methyl-2-propynyl group], 1-methyl-2-propynyl 2,3,4,6-tetrafluorobenzoate [$R^{11}$=$R^{12}$=$R^3$=$R^5$=fluorine atom, $R^{14}$=hydrogen atom, $L^2$=1-methyl-2-propynyl group], 1-methyl-2-propynyl 2,3,4,5,6-pentafluorobenzoate [$R^{11}$=$R^{12}$=$R^{13}$=$R^{14}$=$R^{15}$=fluorine atom, $L^2$=1-methyl-2-propynyl group], 1-methyl-2-butynyl 2-fluorobenzoate [$R^{11}$=fluorine atom, $R^{12}$=$R^{13}$=$R^{14}$=$R^{15}$=hydrogen atom, $L^2$=1-methyl-2-butynyl group], 1-methyl-2-butynyl 3-fluorobenzoate [$R^{12}$=fluorine atom, $R^{11}$=$R^{13}$=$R^{14}$=$R^{15}$=hydrogen atom, $L^2$=1-methyl-2-butynyl group], 1-methyl-2-butynyl 4-fluorobenzoate [$R^{13}$=fluorine atom, $R^{11}$=$R^{12}$=$R^{14}$=$R^{15}$=hydrogen atom, $L^2$=1-methyl-2-butynyl group], 1-methyl-2-butynyl 2,4-difluorobenzoate [$R^{11}$=$R^{13}$=fluorine atom, $R^{12}$=$R^4$=$R^5$=hydrogen atom, $L^2$=1-methyl-2-butynyl group], 1-methyl-2-butynyl 2,6-difluorobenzoate [$R^{11}$=$R^{15}$=fluorine atom, $R^{12}$=$R^{13}$=$R^{14}$=hydrogen atom, $L^2$=1-methyl-2-butynyl group], 1-methyl-2-butynyl 2,4,6-trifluorobenzoate [$R^{11}$=$R^{13}$=$R^{15}$=fluorine atom, $R^{12}$=$R^{14}$=hydrogen atom, $L^2$=1-methyl-2-butynyl group], 1-methyl-2-butynyl 2,3,4,6-tetrafluorobenzoate [$R^1$=$R^2$=$R^{13}$=$R^{15}$=fluorine atom, $R^{14}$=hydrogen atom, $L^2$=1-methyl-2-butynyl group], 1-methyl-2-butynyl 2,3,4,5,6-pentafluorobenzoate [$R^{11}$=$R^{12}$=$R^{13}$=$R^{14}$=$R^{15}$=fluorine atom, $L^2$=1-methyl-2-butynyl], 1,1-dimethyl-2-propynyl 2-fluorobenzoate [$R^{11}$=fluorine atom, $R^{12}$=$R^{13}$=$R^{14}$=$R^{15}$=hydrogen atom, $L^2$=1,1-dimethyl-2-propynyl group], 1,1-dimethyl-2-propynyl 3-fluorobenzoate [$R^{12}$=fluorine atom, $R^1$=$R^3$=$R^{14}$=$R^{15}$=hydrogen atom, $L^2$=1,1-dimethyl-2-propynyl group], 1,1-dimethyl-2-propynyl 4-fluorobenzoate [$R^{13}$=fluorine atom, $R^1$=$R^{12}$=$R^{14}$=$R^{15}$=hydrogen atom, $L^2$=1,1-dimethyl-2-propynyl group], 1,1-dimethyl-2-propynyl 2,4-difluorobenzoate [$R^{11}$=$R^{13}$=fluorine atom, $R^{12}$=$R^{14}$=$R^{15}$=hydrogen atom, $L^2$=1,1-dimethyl-2-propynyl group], 1,1-dimethyl-2-propynyl 2,6-difluorobenzoate [$R^{11}$=$R^1$=fluorine atom, $R^{12}$=$R^{13}$=$R^{14}$=hydrogen atom, $L^2$=1,1-dimethyl-2-propynyl group], 1,1-dimethyl-2-propynyl 2,4,6-trifluorobenzoate [$R^{11}$=$R^{13}$=$R^{15}$=fluorine atom, $R^{12}$=$R^{14}$=hydrogen atom, $L^2$=1,1-dimethyl-2-propynyl group], 1,1-dimethyl-2-propynyl 2,3,4,6-tetrafluorobenzoate [$R^{11}$=$R^{12}$=$R^{13}$=$R^{15}$=fluorine atom, $R^{14}$=hydrogen atom, $L^2$=1,1-dimethyl-2-propynyl group], 1,1-dimethyl-2-propynyl 2,3,4,5,6-pentafluorobenzoate [$R^{11}$=$R^{12}$=$R^{13}$=$R^{14}$=$R^{15}$=fluorine atom, $L^2$=1,1-dimethyl-2-propynyl group], etc.

Aromatic esters include phenyl 2-fluorobenzoate [$R^1$=fluorine atom, $R^{12}$=$R^{13}$=$R^{14}$=$R^{15}$=hydrogen atom, $L^2$=phenyl group], phenyl 3-fluorobenzoate [$R^{12}$=fluorine atom, $R^{11}$=$R^{13}$=$R^{14}$=$R^{15}$=hydrogen atom, $L^2$=phenyl group], phenyl 4-fluorobenzoate [$R^{13}$=fluorine atom, $R^{11}$=$R^{12}$=$R^{14}$=$R^{15}$=hydrogen atom, $L^2$=phenyl group], phenyl 2,4-difluorobenzoate [$R^{11}$=$R^{13}$=fluorine atom, $R^{12}$=$R^{14}$=$R^{15}$=hydrogen atom, $L^2$=phenyl group], phenyl 2,6-difluorobenzoate [$R^{11}$=$R^{15}$=fluorine atom, $R^{12}$=$R^{13}$=$R^{14}$=hydrogen atom, $L^2$=phenyl group], phenyl 2,4,6-trifluorobenzoate [$R^{11}$=$R^{13}$=$R^{15}$=fluorine atom, $R^{12}$=$R^{14}$=hydrogen atom, $L^2$=phenyl group], phenyl 2,3,4,6-tetrafluorobenzoate [$R^{11}$=$R^{12}$=$R^{13}$=$R^{15}$=fluorine atom, $R^{14}$=hydrogen atom, $L^2$=phenyl group], phenyl 2,3,4,5,6-pentafluorobenzoate [$R^{11}$=$R^{12}$=$R^{13}$=$R^{14}$=$R^{15}$=fluorine atom, $L^2$=phenyl group], tolyl 2-fluorobenzoate [$R^{11}$=fluorine atom, $R^{12}$=$R^{13}$=$R^{14}$=$R^{15}$=hydrogen atom, $L^2$=tolyl group], tolyl 3-fluorobenzoate [$R^{12}$=fluorine atom, $R^{11}$=$R^{13}$=$R^{14}$=$R^s5$=hydrogen atom, $L^2$=tolyl group], tolyl 4-fluorobenzoate [$R^{13}$=fluorine atom, $R^{11}$=$R^{12}$=$R^{14}$=$R^{15}$=hydrogen atom, $L^2$=tolyl group], tolyl 2,4-difluorobenzoate [$R^{11}$=$R^{13}$=fluorine atom, $R^{12}$=$R^{14}$=$R^{15}$=hydrogen atom, $L^2$=tolyl group], tolyl 2,6-difluorobenzoate [$R^{11}$=$R^{15}$=fluorine atom, $R^{12}$=$R^{13}$=$R^{14}$=hydrogen atom, $L^2$=tolyl group], tolyl 2,4,6-trifluorobenzoate [$R^{11}$=$R^{13}$=$R^{15}$=fluorine atom, $R^{12}R^{14}$=hydrogen atom, $L^2$=tolyl group], tolyl 2,3,4,6-tetrafluorobenzoate [$R^{11}$=$R^{12}$=$R^{13}$=$R^{15}$=fluorine atom, $R^{14}$=hydrogen atom, $L^2$=tolyl group], tolyl 2,3,4,5,6-pentafluorobenzoate [$R^{11}$=$R^{12}$=$R^{13}$=$R^{14}$=$R^{15}$=fluorine atom, L²=tolyl group], xylyl 2-fluorobenzoate [R¹¹=fluorine atom, R¹²=R¹³=R¹⁴=R¹⁵=hydrogen atom, L²=xylyl group], xylyl 3-fluorobenzoate [R¹²=fluorine atom, R¹¹=R¹³=R¹⁴=R¹⁵=hydrogen atom, L²=xylyl group], xylyl 4-fluorobenzoate [R¹³=fluorine atom, R¹¹=R¹²=R¹⁴=R¹⁵=hydrogen atom, L²=xylyl group], xylyl 2,4-difluorobenzoate [R¹¹=R¹³=fluorine atom, R¹²=R¹⁴=R¹⁵=hydrogen atom, L²=xylyl group], xylyl 2,6-difluorobenzoate [R¹¹=R¹⁵=fluorine atom, R¹²=R¹³=R¹⁴=hydrogen atom, L²=xylyl group], xylyl 2,4,6-trifluorobenzoate [R¹¹=R¹³=R¹⁵=fluorine atom, R¹²SR¹⁴=hydrogen atom, L²=xylyl group], xylyl 2,3,4,6-tetrafluorobenzoate [R¹¹=R¹²=R¹³=R¹⁵=fluorine atom, R⁴=hydrogen atom, L²=xylyl group], xylyl 2,3,4,5,6-pentafluorobenzoate [R¹¹=R¹²=R¹³=R¹⁴=R¹⁵=fluorine atom, L²=xylyl group], mesityl 2-fluorobenzoate [R¹¹=fluorine atom, R¹²=R¹³=R¹⁴=R¹⁵=hydrogen atom, L²=mesityl group], mesityl 3-fluorobenzoate [R¹²=fluorine atom, R¹¹=R¹³=R¹⁴=R⁵=hydrogen atom, L²=mesityl group], mesityl 4-fluorobenzoate [R¹³=fluorine atom, R¹¹=R¹²=R¹⁴=R¹⁵=hydrogen atom, L²=mesityl group], mesityl 2,4-difluorobenzoate [R¹¹=R¹³=fluorine atom, R¹²=R¹⁴=R¹⁵=hydrogen atom, L²=mesityl group], mesityl 2,6-difluorobenzoate [R¹¹=R¹⁵=fluorine atom, R¹²=R¹³=R¹⁴=hydrogen atom, L²=mesityl group], mesityl 2,4,6-trifluorobenzoate [R¹¹=R¹³=R¹⁵=fluorine atom, R¹²=R¹⁴=hydrogen atom, L²=mesityl group], mesityl 2,3,4,6-tetrafluorobenzoate [R¹¹=R¹²=R¹³=R¹⁵=fluorine atom, R¹⁴=hydrogen atom, L²=mesityl group], mesityl 2,3,4,5,6-pentafluorobenzoate [R¹¹=R¹²=R¹³=R¹⁴=R¹⁵=fluorine atom, L²=mesityl group], fluorophenyl 2-fluorobenzoate [R¹¹=fluorine atom, R¹²=R¹³=R¹⁴=R¹⁵=hydrogen atom, L²=fluorophenyl group], fluorophenyl 3-fluorobenzoate [R¹²=fluorine atom, R¹¹=R¹³=R¹⁴=R¹⁵=hydrogen atom, L²=fluorophenyl group], fluorophenyl 4-fluorobenzoate [R¹³=fluorine atom, R¹¹=R¹²=R¹⁴=R¹⁵=hydrogen atom, L²=fluorophenyl group], fluorophenyl 2,4-difluorobenzoate [R¹¹=R¹³=fluorine atom, R¹²=R¹⁴=R¹⁵=hydrogen atom, L²=fluorophenyl group], fluorophenyl 2,6-difluorobenzoate [R¹¹=R¹⁵=fluorine atom, R¹²=R¹³=R¹⁴=hydrogen atom, L²=fluorophenyl group], fluorophenyl 2,4,6-trifluorobenzoate [R¹¹=R¹³=R¹⁵=fluorine atom, R¹²=R¹⁴=hydrogen atom, L²=fluorophenyl group], fluorophenyl 2,3,4,6-tetrafluorobenzoate [R¹¹=R¹²=R¹³=R¹⁵=fluorine atom, R¹⁴=hydrogen atom, L²=fluorophenyl group], fluorophenyl 2,3,4,5,6-pentafluorobenzoate [R¹¹=R¹²=R¹³=R¹⁴=R¹⁵=fluorine atom, L²=fluorophenyl group], biphenyl 2-fluorobenzoate [R¹¹=fluorine atom, R¹²=R¹³=R¹⁴=R¹⁵=hydrogen atom, L²=biphenyl group], biphenyl 3-fluorobenzoate [R¹²=fluorine atom, R¹¹=R¹³=R¹⁴=R¹⁵=hydrogen atom, L²=biphenyl group], biphenyl 4-fluorobenzoate [R¹³=fluorine atom, R¹¹=R¹²=R¹⁴=R¹⁵=hydrogen atom, L²=biphenyl group], biphenyl 2,4-difluorobenzoate [R¹¹=R¹³=fluorine atom, R¹²=R¹⁴=R¹⁵=hydrogen atom, L²=biphenyl group], biphenyl 2,6-difluorobenzoate [R¹¹=R¹⁵=fluorine atom, R¹²=R¹³=R¹⁴=hydrogen atom, L²=biphenyl group], biphenyl 2,4,6-trifluorobenzoate [R¹¹=R¹³=R¹⁵=fluorine atom, R¹²=R¹⁴=hydrogen atom, L²=biphenyl group], biphenyl 2,3,4,6-tetrafluorobenzoate [R¹¹=R¹²=R¹³=R¹⁵=fluorine atom, R¹⁴=hydrogen atom, L²=biphenyl group], biphenyl 2,3,4,5,6-pentafluorobenzoate [R¹¹=R¹²=R¹³=R¹⁴=R¹⁵=fluorine atom, L²=biphenyl group], etc.

Of those, preferred are vinyl 2,4-difluorobenzoate, vinyl 2,6-difluorobenzoate, vinyl 2,4,6-trifluorobenzoate, vinyl 2,3,4,5,6-pentafluorobenzoate, 2-propenyl 2,4-difluorobenzoate, 2-propenyl 2,6-difluorobenzoate, 2-propenyl 2,4,6-trifluorobenzoate, 2-propenyl 2,3,4,5,6-pentafluorobenzoate, 2-propynyl 2,4-difluorobenzoate, 2-propynyl 2,6-difluorobenzoate, 2-propynyl 2,4,6-trifluorobenzoate and 2-propynyl 2,3,4,5,6-pentafluorobenzoate, as enabling increased initial capacity and enhanced cycle property.

[Compound Represented by General Formula (IV)]

The compound to be in the nonaqueous electrolytic solution in the present invention is represented by the following general formula (IV):

[Formula 9]

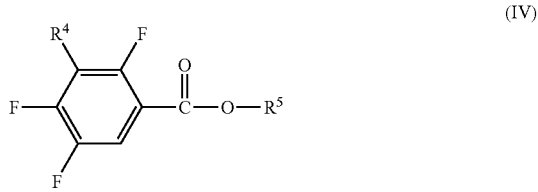

(IV)

(wherein R⁴ represents a methoxy group or an ethoxy group; R⁵ represents a linear or branched alkyl group having from 1 to 6 carbon atoms, a linear or branched alkenyl group having from 2 to 6 carbon atoms, a linear or branched alkynyl group having from 3 to 6 carbon atoms, a phenyl group or a biphenyl group).

R⁴ in the above-mentioned general formula (IV) is a methoxy group or an ethoxy group, preferably a methoxy group.

The linear or branched alkyl group having from 1 to 6 carbon atoms for R⁵ includes a methyl group, an ethyl group, a 1-propyl group, a 2-propyl group, a 1-butyl group, a sec-butyl group, an iso-butyl group, a tert-butyl group, a 1-pentyl group, a tert-pentyl group, a hexyl group.

The linear or branched alkenyl group having from 2 to 6 carbon atoms for R⁵ includes a vinyl group, a 2-propenyl group, a 2-butenyl group, a 3-butenyl group, a 4-pentenyl group, etc.; the linear or branched alkynyl group having from 3 to 6 carbon atoms includes a 2-propynyl group, a 2-butynyl group, a 3-butynyl group, a 4-pentynyl group, a 5-hexynyl group, a 1-methyl-2-propynyl group, etc.

The phenyl group for R⁵ may be substituted with an alkyl group having from 1 to 6 carbon atoms or a fluorine atom, including a phenyl group, a tolyl group, a xylyl group, a mesityl group, a fluorophenyl group, etc. The biphenyl group may be substituted with an alkyl group having from 1 to 6 carbon atoms or a fluorine atom.

Of those, R⁵ preferably has an alkyl group having from 1 to 3 carbon atoms for the reason that the compound may form a tight film on the surface of a negative electrode to thereby prevent the reductive decomposition of an electrolytic solution in charge-discharge cycles, most preferably having a methyl group or an ethyl group.

The ester compound represented by the general formula (IV) includes, concretely, methyl 3-methoxy-2,4,5-trifluorobenzoate [R⁴=methoxy group, R⁵=methyl group], ethyl 3-methoxy-2,4,5-trifluorobenzoate [R⁴=methoxy group, R⁵=ethyl group], propyl 3-methoxy-2,4,5-trifluorobenzoate [R⁴=methoxy group, R⁵=propyl group], vinyl 3-methoxy-2,4,5-trifluorobenzoate [R⁴=methoxy group, R⁵=vinyl group], 2-propenyl 3-methoxy-2,4,5-trifluorobenzoate [R⁴=methoxy group, R⁵=2-propenyl group], 2-butenyl 3-methoxy-2,4,5-trifluorobenzoate [R⁴=methoxy group, R⁵=2-butenyl group], 3-butenyl 3-methoxy-2,4,5-trifluorobenzoate [R⁴=methoxy group, R⁵=3-butenyl group], 4-pentenyl 3-methoxy-2,4,5-trifluorobenzoate [$R^4$=methoxy group, $R^5$=4-pentenyl group], 2-propynyl 3-methoxy-2,4,5-trifluorobenzoate [$R^4$=methoxy group, $R^5$=2-propynyl group], 2-butynyl 3-methoxy-2,4,5-trifluorobenzoate [$R^4$=methoxy group, $R^5$=2-butynyl group], 4-pentynyl 3-methoxy-2,4,5-trifluorobenzoate [$R^4$=methoxy group, $R^5$=4-pentynyl group], 5-hexynyl 3-methoxy-2,4,5-trifluorobenzoate [$R^4$=methoxy group, $R^5$=5-hexynyl group], 1-methyl-2-propynyl 3-methoxy-2,4,5-trifluorobenzoate [$R^4$=methoxy group, $R^5$=1-methyl-2-propynyl group], phenyl 3-methoxy-2,4,5-trifluorobenzoate [$R^4$=methoxy group, $R^5$=phenyl group], tolyl 3-methoxy-2,4,5-trifluorobenzoate [$R^4$=methoxy group, $R^5$=tolyl group], xylyl 3-methoxy-2,4,5-trifluorobenzoate [$R^4$=methoxy group, $R^5$=xylyl group], biphenyl 3-methoxy-2,4,5-trifluorobenzoate [$R^4$=methoxy group, $R^5$=biphenyl group], etc.

Of those, preferred are methyl 3-methoxy-2,4,5-trifluorobenzoate, ethyl 3-methoxy-2,4,5-trifluorobenzoate, vinyl 3-methoxy-2,4,5-trifluorobenzoate, 2-propenyl 3-methoxy-2,4,5-trifluorobenzoate, 2-propynyl 3-methoxy-2,4,5-trifluorobenzoate, phenyl 3-methoxy-2,4,5-trifluorobenzoate, tolyl 3-methoxy-2,4,5-trifluorobenzoate, biphenyl 3-methoxy-2,4,5-trifluorobenzoate; and more preferred are methyl 3-methoxy-2,4,5-trifluorobenzoate, and ethyl 3-methoxy-2,4,5-trifluorobenzoate.

[Nonaqueous Electrolytic Solution]

The first nonaqueous electrolytic solution of the present invention is a nonaqueous electrolytic solution of an electrolyte salt dissolved in a nonaqueous solvent, which contains an ester compound represented by the above-mentioned general formula (III) in an amount of from 0.01 to 10% by weight.

[Formula 10]

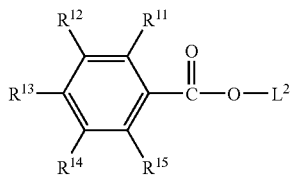

(III)

(wherein $R^{11}$ to $R^{15}$ and $L^2$ have the same meanings as above).

In the nonaqueous electrolytic solution of the present invention, when the content of the ester compound represented by the general formula (III) is more than 10% by weight, then the battery capacity may lower; and when it is less than 0.01% by weight, then the film formation may be insufficient and the initial battery capacity may be poor. Accordingly, the content of the compound is preferably at least 0.01% by weight of the nonaqueous electrolytic solution, more preferably at least 0.1% by weight, even more preferably at least 0.2% by weight, most preferably at least 0.3% by weight. The uppermost limit of the content is preferably at most 10% by weight, more preferably at most 7% by weight, even more preferably at most 5% by weight, most preferably at most 3% by weight.

The second nonaqueous electrolytic solution of the present invention is a nonaqueous electrolytic solution of an electrolyte salt dissolved in a nonaqueous solvent, which contains an ester compound represented by the following general formula (II) and/or (IV), in an amount of from 0.01 to 10% by weigh of the nonaqueous electrolytic solution.

[Formula 11]

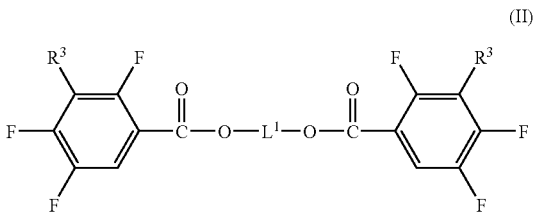

(II)

(wherein $R^3$ and $L^1$ have the same meanings as above)

[Formula 12]

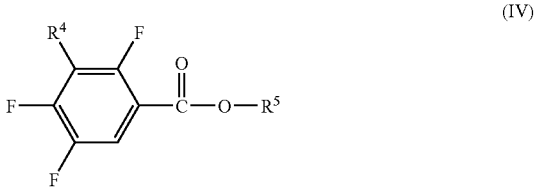

(IV)

(wherein $R^4$ and $R^5$ have the same meanings as above)

In the nonaqueous electrolytic solution of the present invention, when the content of the ester compound represented by the general formula (II) and/or (IV) is more than 10% by weight, then the battery capacity may lower; and when it is less than 0.01% by weight, then the film formation may be insufficient and the battery capacity may be poor. Accordingly, the content of the compound is preferably at least 0.01% by weight of the nonaqueous electrolytic solution, more preferably at least 0.1% by weight, even more preferably at least 0.2% by weight, most preferably at least 0.3% by weight. The uppermost limit of the content is preferably at most 10% by weight, more preferably at most 7% by weight, even more preferably at most 5% by weight, most preferably at most 3% by weight.

[Nonaqueous Solvent]

The nonaqueous solvent to be used in the nonaqueous electrolytic solution of the present invention includes cyclic carbonates, linear carbonates, linear esters, ethers, amides, phosphates, sulfones, lactones, nitriles, S=O bond-containing compounds, etc.

The cyclic carbonates include ethylene carbonate (EC), propylene carbonate (PC), butylene carbonate (BC), fluoroethylene carbonate (FEC), vinylene carbonate (VC), dimethylvinylene carbonate, vinylethylene carbonate, etc. One or more these cyclic carbonates may be used. Especially preferably, the electrolytic solution contains at least two selected from EC, PC, VC and FEC having a high dielectric constant, as its electroconductivity increases and the cycle property are bettered. In particular, the electrolytic solution preferably contains from 3 to 4 different types of such cyclic carbonates as combined.

The content of the cyclic carbonate is preferably within a range of from 10 to 40% by volume of the total volume of the nonaqueous solvent. When the content is less than 10% by volume, then the electroconductivity of the electrolytic solution lowers and the cycle property may worsen; but when the content is more than 40% by volume, then the viscosity of the electrolytic solution may increase and the cycle property may also worsen. Therefore the above-mentioned range is preferred.

The linear carbonates include asymmetric linear carbonates such as methyl ethyl carbonate (MEC), methyl propyl carbonate, methyl isopropyl carbonate, methyl butyl carbonate, ethyl propyl carbonate, etc.; and symmetric linear carbonates such as dimethyl carbonate (DMC), diethyl carbonate (DEC), dipropyl carbonate, dibutyl carbonate, etc. Especially preferred are asymmetric carbonates, as capable of enhancing the cycle property.

One of these linear carbonates may be used; however, preferably, two or more of them are used, as combined, as capable of enhancing the cycle property.

The content of the linear carbonate is preferably within a range of from 60 to 90% by volume of the total volume of the nonaqueous solvent. When the content is less than 60% by volume, then the viscosity of the electrolytic solution may increase and the cycle property may also worsen. When the content is more than 90% by volume, then the electroconductivity of the electrolytic solution lowers and the cycle property may worsen. Therefore the above-mentioned range is preferred.

The linear esters include methyl propionate, methyl pivalate, butyl pivalate, hexyl pivalate, octyl pivalate, dimethyl oxalate, ethyl methyl oxalate, diethyl oxalate, etc. The ethers include tetrahydrofuran, 2-methyltetrahydrofuran, 1,3-dioxane, 1,4-dioxane, 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include divinyl sulfone, sulforlane, etc.; the lactones include γ-butyrolactone, γ-valerolactone, α-angelica-lactone, etc.; the nitriles include acetonitrile, succinonitrile, adiponitrile, etc. Combination of these nitriles and S=O bond-containing compounds is preferred for use herein, as capable of enhancing the cycle property.

Specific examples of the S=O bond-containing compounds include 1,3-propanesultone (PS), 1,4-propanesultone, 1,3-butanediol dimethanesulfonate, 1,4-butanediol dimethanesulfonate, divinyl sulfone, ethylene sulfite, propylene sulfite, vinylethylene sulfite, vinylene sulfite, methyl 2-propynyl sulfite, ethyl 2-propynyl sulfite, dipropynyl sulfite, cyclohexyl sulfite, ethylene sulfate, propylene sulfate, etc.

In general, the above-mentioned nonaqueous solvents are combined for use herein for the purpose of attaining suitable physical properties. The combination includes, for example, a combination of cyclic carbonate and linear carbonate; a combination of cyclic carbonate, linear carbonate and lactone; a combination of cyclic carbonate, linear carbonate and ether; a combination of cyclic carbonate, linear carbonate and linear ester, etc.

Of those, preferred is a combination of cyclic carbonate and linear carbonate, concretely a combination of a cyclic carbonate such as EC, PC, VC, FEC or the like, and a linear carbonate such as DMC, MEC, DEC or the like, as capable of enhancing the cycle property.

The blend ratio of cyclic carbonate and linear carbonate is preferably from 10/90 to 40/60 as a ration of cyclic carbonate/linear carbonate (by volume), from the viewpoint of the ability of enhancing the cycle property, more preferably from 15/85 to 35/65, even more preferably from 20/80 to 30/70.

[Electrolyte Salt]

The electrolyte for use in the present invention includes Li salts such as $LiPF_6$, $LiBF_4$, $LiClO_4$, etc.; linear fluoroalkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso\text{-}C_3F_7)_3$, $LiPF_5(iso\text{-}C_3F_7)$, etc.; and cyclic fluoroalkylene chain-having lithium salts such as $(CF_2)_2(SO_2)_2NLi$, $(CF_2)_3(SO_2)_2NLi$, etc. Of those, especially preferred electrolyte salts are $LiPF_6$, $LiBF_4$, $LiN(SO_2CF_3)_2$, $LiN(SO_2C_2F_5)_2$; and most preferred electrolyte salts are $LiPF_6$, $LiBF_4$ and $LiN(SO_2CF_3)_2$. One or more of these electrolyte salts may be used herein either singly or as combined.

A preferred combination of these electrolyte salts is a combination containing $LiPF_6$ as combined with at least one selected from $LiBF_4$, $LiN(SO_2CF_3)_2$ and $LiN(SO_2C_2F_5)_2$. Preferred are a combination of $LiPF_6$ and $LiBF_4$; a combination of $LiPF_6$ and $LiN(SO_2CF_3)_2$; a combination of $LiPF_6$ and $LiN(SO_2C_2F_5)_2$, etc. When the ratio (by mol) of $LiPF_6/LiBF_4$ or $LiN(SO_2CF_3)_2$ or $LiN(SO_2C_2F_5)_2$ is smaller than 70/30 in point of the proportion of $LiPF_6$, or when the ratio is larger than 99/1 in point of the proportion of $LiPF_6$, then the cycle property may worsen. Accordingly, the ratio (by mol) of $LiPF_6/LiBF_4$ or $LiN(SO_2CF_3)_2$ or $LiN(SO_2C_2F_5)_2$ is preferably within a range of from 70/30 to 99/1, more preferably from 80/20 to 98/2. The combination falling within the above range can enhance the cycle property.

The electrolyte salts may be combined in any desired ratio. In the combination of $LiPF_6$ with any of $LiBF_4$, $LiN(SO_2CF_3)_2$ and $LiN(SO_2C_2F_5)_2$, when the proportion (as ratio by mol) of the other electrolyte salt than those ingredients to the total electrolyte salts is less than 0.01%, then the high-temperature storage stability of the electrolyte mixture may be poor; but when it is more than 45%, then the high-temperature storage stability thereof may worsen. Accordingly, the proportion (as ratio by mol) is preferably from 0.01 to 45%, more preferably from 0.03 to 20%, even more preferably from 0.05 to 10%, most preferably from 0.05 to 5%.

The concentration of all these electrolyte salts as dissolved in the solution is generally preferably at least 0.3 M relative to the above-mentioned nonaqueous solvent, more preferably at least 0.5 M, most preferably at least 0.7 M. The uppermost limit of the concentration is preferably at most 2.5 M, more preferably at most 2.0 M, even more preferably at most 1.5 M, most preferably at most 1.2 M.

[Other Additives]

An aromatic compound may be added to the nonaqueous electrolytic solution of the present invention, thereby securing the safety of the battery in overcharging. Preferred examples of the aromatic compound include cyclohexylbenzene, fluorocyclohexylbenzene compound (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, 1,3-di-tert-butylbenzene, biphenyl, terphenyl(o-, m-, p-), diphenyl ether, fluorobenzene, difluorobenzene (o-, m-, p-), 2,4-difluoroanisole, terphenyl partial hydrolyzate (1,2-dicyclohexylbenzene, 2-phenylbicyclohexyl, 1,2-diphenylcyclohexane, o-cyclohexylbiphenyl), etc. One or more of these aromatic compounds may be used either singly or as combined.

[Production of Nonaqueous Electrolytic Solution]

The nonaqueous electrolytic solution of the present invention can be produced, for example, by mixing the above-mentioned nonaqueous solvents followed by dissolving therein the above-mentioned electrolyte salt and at least one compound selected from those of the above-mentioned general formulae (II), (III) and (IV) in an amount of from 0.01 to 10% by weight of the resulting nonaqueous electrolytic solution.

In this case, the compounds to be added to the nonaqueous solvent and the electrolytic solution are preferably previously purified within a range not significantly detracting from the producibility, in which, therefore, the impurity content is as low as possible.

For example, air or carbon dioxide may be incorporated into the nonaqueous electrolytic solution of the present invention to thereby prevent gas generation resulting from decomposition of electrolytic solution and to enhance the battery characteristics such as the long-term cycle property and the storage property in a charged state.

In the present invention, from the viewpoint of enhancing charging and discharging characteristics at high temperatures, the nonaqueous electrolytic solution preferably contains carbon dioxide as dissolved therein. The amount of carbon dioxide to be dissolved in the nonaqueous electrolytic solution is preferably at least 0.001% by weight of the solution, more preferably at least 0.05% by weight, even more preferably at least 0.2% by weight; and most preferably, carbon dioxide is dissolved in the nonaqueous electrolytic solution until its saturation therein.

[Lithium Secondary Battery]

The lithium secondary battery of the present invention comprises a positive electrode, a negative electrode and the above-mentioned nonaqueous electrolytic solution of an electrolyte salt dissolved in a nonaqueous solvent. The other constitutive components such as a positive electrode and a negative electrode except for the nonaqueous electrolytic solution can be used with no limitation.

For example, as the positive electrode active material, usable are complex metal oxides of lithium containing any of cobalt, manganese or nickel. One or more such positive electrode active materials may be used either singly or as combined.

The complex metal oxides include, for example, $LiCoO_2$, $LiMn_2O_4$, $LiNiO_2$, $LiCO_{1-x}Ni_xO_2$ ($0.01 \leq x \leq 1$), $LiCo_{1/3}Ni_{1/3}Mn_{1/3}O_2$, $LiNi_{1/2}Mn_{3/2}O_4$, $LiCo_{0.98}Mg_{0.02}O_2$, etc. Combinations of $LiCoO_2$ and $LiMn_2O_4$; $LiCoO_2$ and $LiNiO_2$; $LiMn_2O_4$ and $LiNiO_2$ are acceptable herein.

For enhancing safety in overcharging or cycle property, the lithium complex oxide may be partly substituted with any other element for enabling the use of the battery at a charging potential of 4.3 V or more. A part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as $LiCoO_2$, $LiMn_2O_4$ and $LiNiO_2$, with which the positive electrode charging potential in a full-charging state may be 4.3 V or more, based on Li. More preferred are lithium complex oxides usable at 4.4 V or more, such as $LiCO_{1-x}M_xO_2$ (where M is at least one element of Sn, Mg, Fe, Ti, Al, Zr, Cr, V, Ga, Zn and Cu; $0.001 \times 0.05$), $LiCo_{1/3}Ni_{1/3}Mn_{1/3}O_2$, and $LiNi_{1/2}Mn_{3/2}O_4$. When a lithium/transition metal complex oxide having a high charging potential is used, then gas may be generated through reaction with electrolytic solution in charging; however, the lithium secondary battery of the present invention can prevent such gas generation.

Further, lithium-containing olivine-type phosphates are also usable as the positive electrode active material. Their concrete examples include $LiFePO_4$, $LiCoPO_4$, $LiNiPO_4$, $LiMnPO_4$, $LiFe_{1-x}M_xPO_4$ (M is at least one selected from Co, Ni, Mn, Cu, Zn, Nb, Mg, Al, Ti, W, Zr and Cd; and $0 \leq x \leq 0.5$), etc. Of those, preferred are $LiFePO_4$ and $LiCoPO_4$.

The lithium-containing olivine-type phosphate may be combined with, for example, the above-mentioned positive electrode active material.

Not specifically defined, the electroconductive agent of the positive electrode may be any electron-transmitting material not undergoing chemical change. For example, it includes graphites such as natural graphite (flaky graphite, etc.), artificial graphite, etc.; carbon blacks such as acetylene black, ketjen black, channel black, furnace black, lamp black, thermal black, etc. Graphites and carbon blacks may be combined suitably. The amount of the electroconductive agent to be added to the positive electrode mix is preferably from 1 to 10% by weight, more preferably from 2 to 5% by weight.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling-point solvent such as 1-methyl-2-pyrrolidone or the like, and kneading them to give a positive electrode mix, thereafter applying the positive electrode mix onto an aluminium foil or a stainless lath plate or the like serving as a collector, and drying and shaping it under pressure, and then heat-treating it in vacuum at a temperature of from 50° C. to 250° C. or so for about 2 hours.

As the negative electrode active material, usable are one or more of lithium metal, lithium alloys, carbon materials and metal compounds capable of absorbing and releasing lithium, as combined.

Of those, preferred are high-crystalline carbon materials such as artificial graphite, natural graphite or the like of which the ability of absorbing and releasing lithium ions is good. More preferred is a carbon material having a graphite-type crystal structure where the lattice (002) spacing ($d_{002}$) is at most 0.340 nm (nanometers), especially from 0.335 to 0.337 nm. More preferably, the high-crystalline carbon material is coated with a low-crystalline carbon material, as capable of more effectively preventing gas generation. When such a high-crystalline carbon material is used, then it may react with an electrolytic solution in charging to generate gas; however, the lithium secondary battery of the present invention can prevent the reaction.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the capacity of the battery.

The negative electrode may be formed, using the same electroconductive agent, binder and high-boiling point solvent as in the formation of the above-mentioned positive electrode. These are mixed and kneaded to give a negative electrode mix, then the negative electrode mix is applied onto a copper foil or the like serving as a collector, then dried and shaped under pressure, and thereafter heat-treated in vacuum at a temperature of from 50° C. to 250° C. or so for about 2 hours.

In the present invention, preferably, the electrode mixture density is increased for the purpose of enhancing the effect of the ester compound of the above-mentioned general formula (II), (III) and (IV) added to the mixture. In particular, when a lithium complex metal oxide with any of cobalt, manganese or nickel is used as the active material for the positive electrode to be formed on an aluminium foil, then the density of the positive electrode (positive electrode mixture layer) is preferably at least 3.2 g/cm$^3$, more preferably at least 3.3 g/cm$^3$, most preferably at least 3.4 g/cm$^3$. When its uppermost limit is over 4.0 g/cm$^3$, then the electrode is substantially difficult to form. Accordingly, the uppermost limit is preferably at most 4.0 g/cm$^3$, more preferably at most 3.9 g/cm$^3$, most preferably at most 3.8 g/cm$^3$.

When a lithium-containing olivine-type phosphate is used as the positive electrode active material, then the density of the positive electrode (positive electrode mixture layer) is preferably at least 1.3 g/cm$^3$, more preferably at least 1.4 g/cm$^3$, most preferably at least 1.5 g/cm$^3$. When its uppermost limit is over 4.0 g/cm$^3$, then the electrode is substantially difficult to form. Accordingly, the uppermost limit is preferably at most 4.0 g/cm$^3$, more preferably at most 3.5 g/cm$^3$, most preferably at most 3.0 g/cm$^3$.

On the other hand, the density of the negative electrode (negative electrode mixture layer) formed on a copper foil is preferably at least 1.3 g/cm$^3$, more preferably at least 1.4 g/cm$^3$, most preferably at least 1.5 g/cm$^3$. When its uppermost limit is over 2.0 g/cm$^3$, then the electrode is substantially difficult to form. Accordingly, the uppermost limit is preferably at most 2.0 g/cm$^3$, more preferably at most 1.9 g/cm$^3$, most preferably at most 1.8 g/cm$^3$.

Regarding the thickness of the positive electrode layer (per one surface of collector), when the thickness of the electrode material layer is too thin, then the active material amount in the electrode material layer may lower and the battery capacity may be low. Accordingly, the thickness is preferably at least 30 μm, more preferably at least 50 μm. However, when the thickness is too large, then it is unfavorable since the cycle property and the rate property of the battery may worsen. Accordingly, the thickness of the positive electrode layer is preferably at most 120 μm, more preferably at most 100 μm.

When the thickness of the negative electrode layer (per one surface of collector) is too thin, then the active material amount in the electrode material layer may lower and the battery capacity may be low. Accordingly, the thickness is preferably at least 1 μm, more preferably at least 3 μm. However, when the thickness is too large, then it is unfavorable since the cycle property and the rate property of the battery may worsen. Accordingly, the thickness of the negative electrode layer is preferably at most 100 μm, more preferably at most 70 μm.

Also preferably, the positive and negative electrodes in the present invention may be in such a form that the corresponding electrode mixtures are separately applied onto each surface of a collector. In this case, the layer on one surface may be a single layer or a multiple layer. In case where the layer on one surface is a multiple layer, it may comprise two or more, positive electrode active material (or negative electrode active material)-containing layers. A more preferred constitution comprises a positive electrode active material (or negative electrode active material)-containing layer and a positive electrode active material (or negative electrode active material)-free layer, in which the positive electrode active material (or negative electrode active material)-free layer may be a protective layer for protecting the positive electrode active material (or negative electrode active material)-containing layer, or an interlayer to be between the divided positive electrode active material (or negative electrode active material)-containing layer, or an underlayer to be between the positive electrode active material (or negative electrode active material)-containing layer and the collector, etc. In the present invention, all these are generically referred to as an auxiliary layer.

When the thickness of the auxiliary layer (per one surface) is too thin, the decomposition of the electrolytic solution could not be prevented; and therefore, the thickness is preferably at least 1 μm, more preferably at least 3 μm. However, when the thickness is too large, then it is unfavorable since the layer may interfere with ion movement and the cycle property and the rate property may be thereby worsened. Accordingly, the thickness of the auxiliary layer is preferably at most 20 μm, more preferably at most 10 μm.

Especially preferably in the present invention, the battery structure has a protective layer for the purpose of enhancing the effect of the ester compound of the above-mentioned general formula (II), (III) and (IV) added thereto. Preferably, the protective layer is on both of the positive and negative electrode or on any of the positive and negative electrode; and more preferably, the protective layer is to protect the negative electrode. The protective layer comprises at least one layer, and may comprise plural layers that are the same or different. The protective layer may be formed of water-insoluble particles, a binder, etc., in which the binder may be the same as that for use in producing the above-mentioned electrode mixture. The water-insoluble particles are preferably those poorly reactive with alkali metal, especially lithium, for which usable is at least one type of various electroconductive particles, substantially non-conductive organic or inorganic particles. The proportion of the insoluble particles to be in the protective layer is preferably from 2.5% by weight to 99% by weight, more preferably from 5% by weight to 98% by weight.

The water-insoluble electroconductive particles include metals, metal oxides, metal fibers, carbon fibers, and carbon particles of carbon black, graphite or the like. The non-conductive water-insoluble particles include Teflon® fine powders, SiC, aluminium nitride, alumina, zirconia, magnesia, mullite, forsterite, steatite, etc. Of those water-insoluble particles, especially preferred are ceramic particles of SiC, aluminium nitride, alumina, zirconia, magnesia, mullite, forsterite, steatite or the like; and these may be used either singly or as combined with carbon particles for making the protective layer electroconductive. The carbon particles to be used as the electroconductive material may be any known carbon materials. Concretely, usable are the electroconductive agents that are used in preparing the electrode mixture. Regarding their morphology, the particles may be needle-like, columnar, tabular or massive; and preferably, their maximum diameter is from 0.02 μm to 20 μm, more preferably from 0.1 μm to 10 μm.

The lithium secondary battery can have any structure without restriction. The secondary battery may be a coin-shaped battery, a cylindrical battery, a square-shaped battery, or a laminate-type battery, each having a single layered or multi-layered separator. The battery separator may be composed of a single layered or laminated porous film, woven fabric, or non-woven fabric of a polyolefin such as polypropylene or polyethylene.

A separator having a significantly high Gurley value (air permeability) may lead to a reduction in lithium ion conductivity and thus does not sufficiently function as a battery separator, although it depends on fabrication conditions. Therefore, the Gurley value is preferably 1000 seconds/100 cc or lower, more preferably 800 seconds/100 cc or lower, and most preferably 500 seconds/100 cc or lower. A significantly low Gurley value of the battery separator may lead to low mechanical strength. Therefore, the Gurley value is preferably 50 seconds/100 cc or more, more preferably 100 seconds/100 cc or more, and most preferably 300 seconds/100 cc or more. The porosity of the separator preferably ranges from 30% to 60%, more preferably from 35% to 55%, and most preferably from 40% to 50%, from the viewpoint of improvements in capacity characteristics of the battery.

Furthermore, a higher energy density is achieved by a smaller thickness of the separator. Thus, the thickness of the battery separator is preferably 50 μm or less, more preferably 40 μm or less, and most preferably 25 μm or less. Also, in order to ensure sufficient mechanical strength, the thickness of the battery separator is preferably 5 μm or more, more preferably 10 μm or more, and most preferably 15 μm or more.

The lithium secondary battery of the present invention exhibits excellent long-term cycle property even when the final charging voltage is 4.2 V or higher and particularly 4.3 V or higher. Furthermore, the cycle property are favorable even when the final charging voltage is 4.4 V. The final discharging voltage can be set to 2.5 V or more and preferably 2.8 V or more. Although the current value is not restricted, a constant current discharge of 0.1 C to 3 C is generally employed. The lithium secondary battery of the present invention may be charged and discharged at −40° C. to 100° C. and preferably 0° C. to 80° C.

In the present invention, a sealing plate may be provided with a relief valve, as a countermeasure against an increase in internal pressure of the lithium secondary battery. Alternatively, a cutout may be provided in a battery component such as a battery can or a gasket.

In the lithium secondary battery of the present invention, a plurality of lithium secondary batteries may be accommodated in a battery pack in series and/or in parallel, as necessary. The battery pack can be provided with an overcurrent circuit breaker, such as a PTC element, a thermal fuse, or a bimetal, as well as a safety circuit (a circuit that can monitor the voltage, the temperature, and the current of each battery and/or the entire battery pack, and can shut off the current, as necessary).

EXAMPLES

Production Examples for the ester compounds of the present invention, and Examples of using the electrolytic solution of the present invention are given below.

Production Example 1

Production of vinyl 3-methoxy-2,4,5-trifluorobenzoate (Compound 2)

[Formula 13]

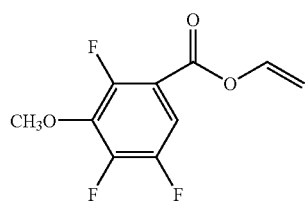

Compound-2

3-Methoxy-2,4,5-trifluorobenzoic acid (MTFBA) (10.19 g, 0.0494 mol), vinyl acetate (85.1 g, 0.989 mol), palladium acetate (1.66 g, 0.00741 mol), and potassium hydroxide (0.277 g, 0.00494 mol) were stirred at 40° C. for 24 hours. The reaction mixture was filtered, the filtrate was washed with saturated $NaHCO_3$ solution, then washed with brine, dried with $MgSO_4$, and concentrated with an evaporator to give a vinyl ester (5.89 g, yield: 51%). This was purified through vacuum distillation (135° C./1.5 Torr), and used in the battery evaluation test.

The structure of the obtained vinyl 3-methoxy-2,4,5-trifluorobenzoate was confirmed through $^1$H-NMR and $^{13}$C-NMR (using JEOL's Model AL300) and through mass spectrometry (using Hitachi's Model M80B). The results are shown below.

(1) $^1$H-NMR (300 MHz, $CDCl_3$): δ=7.9-7.4 (m, 1H), 5.1 (dxd, J=7.0×1.0 Hz, 1H), 4.8 (dxd, J=3.1×0.9 Hz, 1H), 4.1 (t, J=1.2 Hz, 3H).

(2) $^{13}$C-NMR (75 MHz, $CDCl_3$) δ=159.7-159.6 (m), 154.4-145.2 (m), 141.0, 112.4-112.1 (m), 99.4, 62.3 (t, J=3.7 Hz).

(3) mass spectrometry: MS (EI) m/z (%)=232 (10) [M$^+$], 189 (100), 161(27), 146(31), 113(22), 81(9), 43(4), 18 (8).

Production Example 2

Production of allyl 3-methoxy-2,4,5-trifluorobenzoate (Compound 3)

[Formula 14]

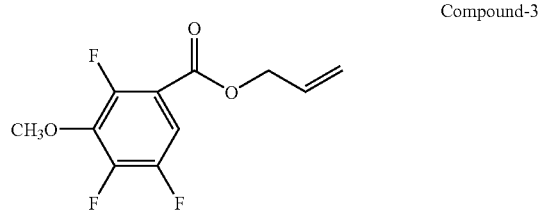

Compound-3

MTFBA (20.42 g, 0.0991 mol) and dimethylformamide (hereinafter referred to as "DMF") (0.0724 g, 0.991 mmol) were dissolved in toluene (100 mL), andthionyl chloride (23.56 g, 0.198 mol) was dropwise added thereto at 70° C., taking 60 minutes. After the addition, this was stirred at 70° C. for 2 hours to confirm the disappearance of MTFBA, and then toluene and the excessive thionyl chloride were removed under reduced pressure, thereby preparing an acid chloride of MTFBA. In a separate reactor, allyl alcohol (6.04 g, 0.104 mol), triethylamine (10.5 g, 0.102 mol) and toluene (30 mL) were mixed, and the prepared acid chloride of MTFBA was dropwise added thereto at 0° C. After the addition, this was stirred at room temperature for 1 hour, then washed with aqueous saturated $NaHCO_3$ solution, and extracted with ethyl acetate. The organic layer was washed twice with brine, then dried with $MgSO_4$, and concentrated with an evaporator to give an allyl ester (20.5 g, yield: 84%). This was purified through vacuum distillation (108° C./2 Torr), and used in the battery evaluation test.

The structure of the obtained allyl 3-methoxy-2,4,5-trifluorobenzoate was confirmed in the same manner as above. The disappearance of MTFBA was confirmed by sampling a predetermined amount of a part of the reaction liquid, adding methanol thereto and quantitatively determining the resulting methyl ester through HPLC (the same shall apply to the following Production Examples). The results are shown below.

(1) $^1$H-NMR (300 MHz, $CDCl_3$): δ=7.5-7.4 (m, 1H), 6.1-5.9 (m, 1H), 5.4 (dxq, J=7.5×1.5 Hz, 1H), 5.3 (dxq, J=5.2×2.1 Hz, 1H), 4.8 (dxt, J=2.8×1.5 Hz, 2H), 4.1 (t, J=1.2 Hz, 3H).

(2) $^{13}$C-NMR (75 MHz, CDCl$_3$) δ=162.4, 154.0-153.9 (m), 150.6-145.1 (m), 131.5, 118.9, 112.3-112.0 (m), 66.4, 62.3 (t, J=3.1 Hz).

(3) mass spectrometry: MS (EI) m/z (%)=246 (11) [M$^+$], 189(100), 116(7), 146(8), 118(7), 81(3), 41(26), 39(15), 18 (6).

Production Example 3

Production of propargyl 3-methoxy-2,4,5-trifluorobenzoate (Compound 4)

[Formula 15]

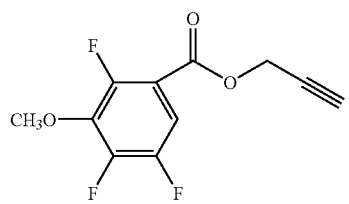

Compound-4

MTFBA (20.11 g, 0.0976 mol) and DMF (0.0713 g, 0.976 mmol) were dissolved in toluene (100 mL), and thionyl chloride (23.21 g, 0.195 mol) was dropwise added thereto at 70° C., taking 60 minutes. After the addition, this was stirred at 70° C. for 2 hours to confirm the disappearance of MTFBA, and then toluene and the excessive thionyl chloride were removed under reduced pressure, thereby preparing an acid chloride of MTFBA. In a separate reactor, propargyl alcohol (5.72 g, 0.102 mol), triethylamine (10.3 g, 0.102 mol) and toluene (30 mL) were mixed, and the prepared acid chloride of MTFBA was dropwise added thereto at 0° C. After the addition, this was stirred at room temperature for 1 hour, then washed with water in the same manner as in Production Example 2, thereby giving a propargyl ester (21.4 g, yield: 90%). This was purified through vacuum distillation (93° C./1 Torr), and used in the battery evaluation test.

The structure of the obtained propargyl 3-methoxy-2,4,5-trifluorobenzoate was confirmed in the same manner as above. The results are shown below.

(1) $^1$H-NMR (300 MHz, CDCl$_3$): δ=7.6-7.5 (m, 1H), 4.9 (d, J=2.4 Hz, 2H), 4.1 (t, J=1.1 Hz, 3H), 2.6 (t, J=4.9 Hz, 1H).

(2) $^{13}$C-NMR (75 MHz, CDCl$_3$): δ=161.9, 154.2-145.2 (m), 112.4-112.0 (m), 77.0, 75.6, 62.3 (t, J=3.4 Hz), 53.1.

(3) mass spectrometry: MS (EI) m/z (%)=224 (17) [M$^+$], 189(100), 161(10), 146(11), 99(11), 68(9), 39(49), 18 (14).

Production Example 4

Production of phenyl 3-methoxy-2,4,5-trifluorobenzoate (Compound 5)

[Formula 16]

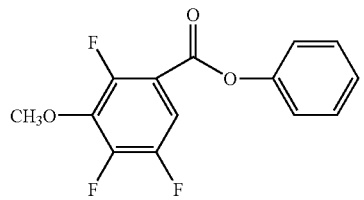

Compound-5

MTFBA (21.33 g, 0.104 mol) and DMF (0.0755 g, 1.04 mmol) were dissolved in toluene (100 mL), and thionyl chloride (24.7 g, 0.208 mol) was dropwise added thereto at 70° C., taking 60 minutes. After the addition, this was stirred at 70° C. for 2 hours to confirm the disappearance of MTFBA, and then toluene and the excessive thionyl chloride were removed under reduced pressure, thereby preparing an acid chloride of MTFBA. In a separate reactor, phenol (10.2 g, 0.109 mol), triethylamine (11.02 g, 0.109 mol) and toluene (45 mL) were mixed, and the prepared acid chloride of MTFBA was dropwise added thereto at 0° C. After the addition, this was stirred at room temperature for 1 hour, then washed with water in the same manner as in Production Example 2, thereby giving a phenyl ester (25.1 g, yield: 86%). This was purified through vacuum distillation (169° C./1.5 Torr), and used in the battery evaluation test.

The structure of the obtained phenyl 3-methoxy-2,4,5-trifluorobenzoate was confirmed in the same manner as above. The results are shown below.

(1) $^1$H-NMR (300 MHz, CDCl$_3$): δ=7.6-7.2 (m, 6H), 4.1 (t, J=1.2 Hz, 3H).

(2) $^{13}$C-NMR (75 MHz, CDCl$_3$): δ=161.2, 154.4-145.2 (m), 153.4, 129.6, 126.4, 121.5, 112.6-112.3 (m), 62.4 (t, J=3.8 Hz).

(3) mass spectrometry: MS (EI) m/z (%)=282 (9) [M$^+$], 189 (100), 161(9), 146(10), 113(6), 81(3), 39 (9).

Production Example 5

Production of biphenyl 3-methoxy-2,4,5-trifluorobenzoate (Compound 6)

[Formula 17]

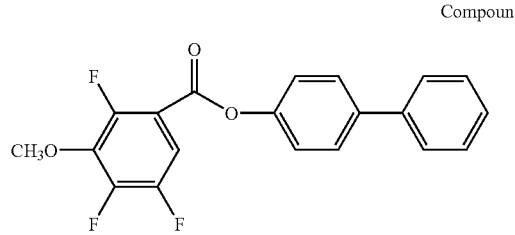

Compound-6

MTFBA (21.33 g, 0.104 mol) and DMF (0.0755 g, 1.04 mmol) were dissolved in toluene (100 mL), and thionyl chloride (24.7 g, 0.208 mol) was dropwise added thereto at 70° C., taking 60 minutes. After the addition, this was stirred at 70° C. for 2 hours to confirm the disappearance of MTFBA, and then toluene and the excessive thionyl chloride were removed under reduced pressure, thereby preparing an acid chloride of MTFBA. In a separate reactor, 4-phenylphenol (18.6 g, 0.109 mol), triethylamine (11.02 g, 0.109 mol), toluene (45 mL) and ether (45 mL) were mixed, and the prepared acid chloride of MTFBA was dropwise added thereto at 0° C. After the addition, this was stirred at room temperature for 1 hour, then washed with aqueous 5%-NaOH solution, and extracted with ethyl acetate. The organic layer was washed twice with brine, dried with MgSO$_4$, and concentrated with an evaporator thereby giving a biphenyl ester (7.8 g, yield: 21%). This was purified through crystallization with a solvent of dimethyl carbonate (white powder, m.p. 94° C.), and used in the battery evaluation test.

The structure of the obtained biphenyl 3-methoxy-2,4,5-trifluorobenzoate was confirmed in the same manner as above. The results are shown below.

(1) $^1$H-NMR (300 MHz, CDCl$_3$): δ=7.7-7.3 (m, 10H), 4.1 (t, J=1.1 Hz, 3H).

(2) $^{13}$C-NMR (75 MHz, CDCl$_3$): δ=161.2, 154.2-145.2 (m), 149.8, 140.2, 139.5, 128.3, 128.3, 127.5, 127.2, 112.5 (d, J=10.6 Hz), 62.4 (d, J=3.7 Hz).

(3) mass spectrometry: MS (EI) m/z (%)=358 (20) [M$^+$], 189(100), 161(7), 146(8), 115(11), 63 (4).

Production Example 6

Production of 2-butyne-1,4-diol bis(3-methoxy-2,4,5-trifluorobenzoate) (Compound 7)

[Formula 18]

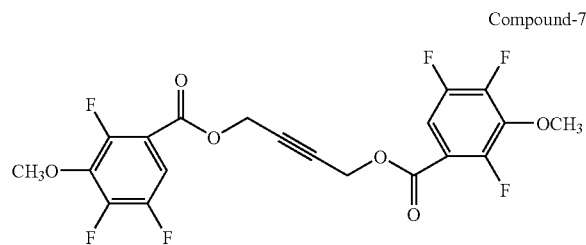

Compound-7

MTFBA (15.07 g, 0.073 mol) and DMF (0.0637 g, 0.731 mmol) were dissolved in toluene (50 mL), and thionyl chloride (13.04 g, 0.110 mol) was dropwise added thereto at 70° C., taking 60 minutes. After the addition, this was stirred at 70° C. for 2 hours to confirm the disappearance of MTFBA, and then toluene and the excessive thionyl chloride were removed under reduced pressure, thereby preparing an acid chloride of MTFBA. In a separate reactor, 2-butyne-1,4-diol (3.12 g, 0.036 mol), triethylamine (7.86 g, 0.078 mol) and toluene (100 mL) and were mixed, and the prepared acid chloride of MTFBA was dropwise added thereto at 0° C. After the addition, this was stirred at room temperature for 1 hour, then washed with water in the same manner as in Production Example 2, thereby giving 2-butyne-1,4-diol bis(3-methoxy-2,4,5-trifluorobenzoate) (16.6 g, yield: 99%). This was purified through crystallization with a solvent of dimethyl carbonate (white powder, m.p. 96° C.), and used in the battery evaluation test.

The structure of the obtained 2-butyne-1,4-diol bis(3-methoxy-2,4,5-trifluorobenzoate) was confirmed in the same manner as above. The results are shown below.

(1) $^1$H-NMR (300 MHz, CDCl$_3$): δ=7.6-7.5 (m, 2H), 4.9 (s, 4H), 4.1 (t, J=1.2 Hz, 6H).

(2) IR (KBr method): 1730, 1621, 1504, 1479, 1438, 1384, 1353, 1276, 1222, 1102, 957, 784, 569 cm$^{-1}$.

(3) mass spectrometry: MS (EI) m/z (%)=462 (5) [M$^+$], 418 (4), 257 (4), 189(100), 146(5), 32 (4).

Example A-1

Preparation of Electrolytic Solution

LiPF$_6$ to be 0.95 M and LiN(SO$_2$ CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume); and further the following Compound-1 was added thereto in an amount of 2% by weight, thereby preparing a nonaqueous electrolytic solution.

[Formula 19]

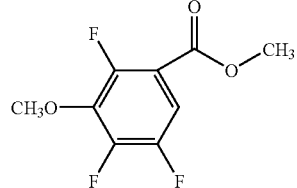

Compound-1

[Production of Lithium Ion Secondary Battery]

LiCO$_{1/3}$Mn$_{1/3}$Ni$_{1/3}$O$_2$ (positive electrode active material) (92% by weight), acetylene black (electroconductive agent) (3% by weight) and polyvinylidene fluoride (binder) (5% by weight) were mixed in that ratio, then a solvent of 1-methyl-2-pyrrolidone was added thereto and mixed. The resulting mixture was applied onto an aluminium foil collector, dried, processed under pressure and cut into a predetermined size, thereby producing a long rectangular, positive electrode sheet. Artificial graphite (negative electrode active material) (95% by weight) and polyvinylidene fluoride (binder) (5% by weight) were mixed in that ratio, and a solvent of 1-methyl-2-pyrrolidone was added thereto and mixed. The resulting mixture was applied onto a copper foil collector, dried, processed under pressure and cut into a predetermined size, thereby producing a long rectangular, negative electrode sheet. The positive electrode sheet, a porous polyethylene film separator, the negative electrode sheet and a separator were laminated in that order, and the resulting laminate was coiled up. The coil was housed into a nickel-plated, iron cylindrical battery can serving also as a negative electrode terminal. Further, the electrolytic solution was injected thereinto, and the can was calked with a battery cap having a positive electrode terminal, via a gasket therebetween, thereby constructing a cylindrical battery having a designed capacity of 2200 mAh. The positive electrode terminal was connected to the positive electrode sheet via an aluminium lead tab therebetween; and the negative electrode can was previously connected to the negative electrode sheet inside the battery, via a nickel lead tab therebetween.

[Determination of Battery Characteristics]
[Determination of Cycle Property]

In a thermostat chamber kept at 25° C., the battery constructed according to the above-mentioned method was charged up to a terminal voltage of 4.35 V for 7 hours with a constant current and a constant voltage of 440 mAh (0.2 C), then this was discharged to a discharge voltage of 2.7 V under the constant current of 440 mAh (0.2 C), and the initial capacity of the battery was thus determined. The battery of which the initial capacity had been determined was further charged, in a thermostat chamber kept at 45° C., up to a terminal voltage of 4.35 V for 3 hours with a constant current and a constant voltage of 2200 mAh (1 C), then this was discharged to a discharge voltage of 2.7 V under the constant current of 2200 mAh (1 C). This is one cycle. The battery was subjected to 100 cycles. After the cycle test, the capacity retention of the battery was determined according to the following formula. As a result, the capacity retention of the battery after 100 cycles was 90%.

Capacity Retention(%)=(discharge capacity after 100 cycles/discharge capacity in 1 cycle)×100.

Examples A-2 to A-7

Like in Example A-1, LiPF$_6$ to be 0.95 M and LiN(SO$_2$ CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume), and in place of adding Compound-1 thereto, any of Compound 2 to Compound 7 was added thereto in an amount of 2% by weight, thereby preparing a nonaqueous electrolytic solution. Using this, a cylindrical battery was constructed, and its battery characteristics were determined. The results are shown in Table A-1.

Examples A-8 to A-11

Like in Example A-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume), and Compound-1 was added thereto in an amount of 0.01% by weight, 1% by weight, 5% by weight or 10% by weight, thereby preparing a nonaqueous electrolytic solution. Using this, a cylindrical battery was constructed, and its battery characteristics were determined. The results are shown in Table A-1.

Comparative Example A-1

Like in Example A-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume); however, Compound-1 was not added thereto. Using the thus-prepared nonaqueous electrolytic solution, a cylindrical battery was constructed, and its battery characteristics were determined. The results are shown in Table A-1.

Comparative Examples A-2 and A-3

Like in Example A-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume), and in place of adding Compound-1 thereto, any of the following Comparative Compound-1 or 2 was added thereto in an amount of 2% by weight, thereby preparing a nonaqueous electrolytic solution. Using this, a cylindrical battery was constructed, and its battery characteristics were determined. The results are shown in Table A-1.

TABLE 1

Table A-1

[Formula 20]

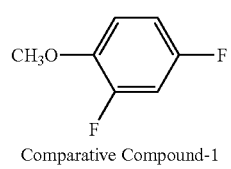

Comparative Compound-1

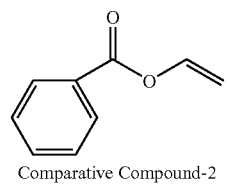

Comparative Compound-2

TABLE 1-continued

| Compound | Amount Added (wt. %) | Initial Discharge Capacity Relative Value (%) | Capacity Retention after 100 cycles (%) |
|---|---|---|---|
| Example A-1 | Compound-1 | 2 | 115 | 90 |
| Example A-2 | Compound-2 | 2 | 110 | 91 |
| Example A-3 | Compound-3 | 2 | 112 | 91 |
| Example A-4 | Compound-4 | 2 | 114 | 89 |
| Example A-5 | Compound-5 | 2 | 107 | 87 |
| Example A-6 | Compound-6 | 2 | 106 | 86 |
| Example A-7 | Compound-7 | 2 | 111 | 90 |
| Example A-8 | Compound-1 | 0.01 | 105 | 84 |
| Example A-9 | Compound-1 | 1 | 110 | 88 |
| Example A-10 | Compound-1 | 5 | 109 | 88 |
| Example A-11 | Compound-1 | 10 | 104 | 80 |
| Comparative Example A-1 | none | — | 100 | 60 |
| Comparative Example A-2 | Comparative Compound-1 | 2 | 90 | 59 |
| Comparative Example A-3 | Comparative Compound-2 | 2 | 102 | 62 |

Example A-12

Like in Example A-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/fluoroethylene carbonate (FEC)/vinylene carbonate (VC)/methyl ethyl carbonate (MEC)=3/10/15/2/70 (by volume); and Compound-1 in an amount of 2% by weight, adiponitrile in an amount of 1% by weight, and cyclohexyl sulfite in an amount of 0.5% by weight were added thereto, thereby preparing a nonaqueous electrolytic solution. Using this, a cylindrical battery was constructed, and its battery characteristics were determined. The results are shown in Table A-2.

Comparative Example A-4

Like in Example A-12, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/fluoroethylene carbonate (FEC)/vinylene carbonate (VC)/methyl ethyl carbonate (MEC)=3/10/15/2/70 (by volume); however, Compound-1, adiponitrile and cyclohexyl sulfite were not added thereto. Using the thus-prepared nonaqueous electrolytic solution, a cylindrical battery was constructed, and its battery characteristics were determined. The results are shown in Table A-2.

TABLE A-2

| | Compound | Amount Added (wt. %) | Initial Discharge Capacity Relative Value (%) | Capacity Retention after 100 cycles (%) |
|---|---|---|---|---|
| Example A-12 | Compound-1 | 2 | 116 | 91 |
| Comparative Example A-4 | none | — | 104 | 63 |

Examples A-1 to A-12 of the present invention where the negative electrode is made of graphite confirm excellent cycle property; and it has been found that, not limited to the graphite negative electrode, the electrolytic solution of the present invention is also effective for a silicon negative electrode, a tin negative electrode and an Li negative electrode, in enhancing the cycle property like in these Examples.

Example B-1

Using LiFePO$_4$ (positive electrode active material) in place of the positive electrode active material used in Example A-1, a positive electrode sheet was produced. LiFePO$_4$ (positive electrode active material) (90% by weight), acetylene black (electroconductive agent) (5% by weight) and polyvinylidene fluoride (binder) (5% by weight) were mixed in that ratio, then a solvent of 1-methyl-2-pyrrolidone was added thereto and mixed. The resulting mixture was applied onto an aluminium foil collector, dried, processed under pressure and cut into a predetermined size, thereby producing a long rectangular, positive electrode sheet. The positive electrode sheet, a porous polyethylene film separator, a negative electrode sheet and a separator were laminated in that order, and the resulting laminate was coiled up. The coil was housed into a nickel-plated, iron-made cylindrical battery can serving also as a negative electrode terminal. Further, the electrolytic solution prepared in Example A-1 was injected thereinto, and the can was calked with a battery cap having a positive electrode terminal, via a gasket therebetween, thereby constructing a cylindrical battery having a planned capacity of 1200 mAh. The positive electrode terminal was connected to the positive electrode sheet via an aluminium lead tab therebetween; and the negative electrode can was previously connected to the negative electrode sheet inside the battery, via a nickel lead tab therebetween.

[Determination of Battery Characteristics]
[Determination of Cycle Property]

In a thermostat chamber kept at 25° C., the battery constructed according to the above-mentioned method was charged up to a terminal voltage of 3.6 V for 7 hours with a constant current and a constant voltage of 240 mAh (0.2 C), then this was discharged to a discharge voltage of 2.0 V under the constant current of 240 mAh (0.2 C), and the initial capacity of the battery was thus determined. The battery of which the initial capacity had been determined was further charged, in a thermostat chamber kept at 45° C., up to a terminal voltage of 3.6 V for 3 hours with a constant current and a constant voltage of 1200 mAh (1 C), then this was discharged to a discharge voltage of 2.0 V under the constant current of 1200 mAh (1 C). This is one cycle. The battery was subjected to 100 cycles. After the cycle test, the capacity Retention of the battery was determined according to the following formula. As a result, the capacity retention of the battery was 83%.

Capacity Retention(%)=(discharge capacity after 100 cycles/discharge capacity in 1 cycle)×100.

Examples B-2 to B-7

Like in Example B-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume), and in place of adding Compound-1 thereto, any of Compound 2 to Compound 7 was added thereto in an amount of 2% by weight, thereby preparing a nonaqueous electrolytic solution in the same manner as in Example B-1. Using this, a cylindrical battery was constructed, and its battery characteristics were determined. The results are shown in Table B-1.

Comparative Example B-1

Like in Example B-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume); however, Compound-1 was not added thereto. Using the thus-prepared nonaqueous electrolytic solution, a cylindrical battery was constructed, and its battery characteristics were determined. The results are shown in Table B-1.

Comparative Examples B-2 to 3

Like in Example B-1, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/dimethyl carbonate (DMC)/diethyl carbonate (DEC)=18/10/2/35/35 (by volume), and in place of adding Compound-1 thereto, any of Comparative Compound-1 or 2 was added thereto in an amount of 2% by weight, thereby preparing a nonaqueous electrolytic solution in the same manner as in Example B-1. Using this, a cylindrical battery was constructed, and its battery characteristics were determined. The results are shown in Table B-1.

TABLE B-1

| | Compound | Amount Added (wt. %) | Initial Discharge Capacity Relative Value (%) | Capacity Retention after 100 cycles (%) |
|---|---|---|---|---|
| Example B-1 | Compound-1 | 2 | 119 | 83 |
| Example B-2 | Compound-2 | 2 | 112 | 84 |
| Example B-3 | Compound-3 | 2 | 114 | 84 |
| Example B-4 | Compound-4 | 2 | 118 | 80 |
| Example B-5 | Compound-5 | 2 | 112 | 78 |
| Example B-6 | Compound-6 | 2 | 113 | 77 |
| Example B-7 | Compound-7 | 2 | 120 | 84 |
| Comparative Example B-1 | none | — | 100 | 50 |
| Comparative Example B-2 | Comparative Compound-1 | 2 | 95 | 51 |
| Comparative Example B-3 | Comparative Compound-2 | 2 | 103 | 53 |

It is known that, as compared with the lithium secondary battery of Comparative Examples not containing the specific ester compound represented by the general formula (II) or (IV), the lithium secondary battery of Examples B-1 to B-7 have more excellent battery performance in point of the initial battery capacity and the cycle property of the battery.

Examples B-1 to B-7 of the present invention where the negative electrode is made of graphite confirm excellent cycle property; and it has been found that, not limited to the graphite negative electrode, the electrolytic solution of the present invention is also effective for a silicon negative electrode, a tin negative electrode and an Li negative electrode, in enhancing the cycle property like in these Examples.

Example C-1

Preparation of Electrolytic Solution

LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC)=8/20/2/35/35 (by volume); and further, propargyl 2,4-difluorobenzoate was added thereto in an amount of 0.5% by weight, thereby preparing a nonaqueous electrolytic solution.

[Production of Lithium Ion Secondary Battery]

LiCoO$_2$ (positive electrode active material) (85% by weight), graphite (electroconductive agent) (10% by weight) and polyvinylidene fluoride (binder) (5% by weight) were mixed in that ratio, then a solvent of 1-methyl-2-pyrrolidone was added thereto and mixed. The resulting mixture was applied onto both surfaces of an aluminium foil (collector), dried, processed under pressure and cut into a predetermined size, thereby producing a long rectangular, positive electrode sheet. Artificial graphite (negative electrode active material) (95% by weight) and polyvinylidene fluoride (binder) (5% by weight) were mixed in that ratio, and a solvent of 1-methyl-2-pyrrolidone was added thereto and mixed. The resulting mixture was applied onto both surfaces of a copper foil (collector), dried, processed under pressure and cut into a predetermined size, thereby producing a long rectangular, negative electrode sheet. The positive electrode sheet, a porous polyethylene film separator, the negative electrode sheet and a separator were laminated in that order, and the resulting laminate was coiled up. The coil was housed into a nickel-plated, iron-made cylindrical battery can serving also as a negative electrode terminal. Further, the electrolytic solution was injected thereinto, and the can was calked with a battery cap having a positive electrode terminal, via a gasket therebetween, thereby constructing a 18650-type cylindrical battery. The positive electrode terminal was connected to the positive electrode sheet via an aluminium lead tab therebetween; and the negative electrode can was previously connected to the negative electrode sheet inside the battery, via a nickel lead tab therebetween.

[Determination of Battery Characteristics]
[Determination of Cycle Property]

In a thermostat chamber kept at 25° C., the battery constructed according to the above-mentioned method was charged up to 4.2 V with a constant current of 1 mA/cm$^2$, and then further charged up to a terminal voltage of 4.35 V for 2.5 hours, and thereafter this was discharged to a discharge voltage of 3.0 V under a constant current of 0.33 mA/cm$^2$, and the initial capacity of the battery was thus determined. The initial efficiency was 85%.

Next, in a thermostat chamber kept at 60° C., the battery was charged up to 4.35 V with a constant current of 1 mA/cm$^2$, then further charged at a constant voltage of 4.35 V for 2.5 hours, and thereafter discharged to a discharge voltage of 3.0 V under a constant current of 1 mA/cm$^2$. This is one cycle. The battery was subjected to 100 cycles. After the cycle test, the capacity retention of the battery was determined according to the following formula. As a result, the capacity retention of the battery after 100 cycles was 85%. The results are shown in Table C-1.

Capacity Retention(%)=(discharge capacity after 100 cycles/discharge capacity in 1 cycle)×100.

Examples C-2 to 11

LiPF$_6$ to be 0.95 M and LiN(SO$_2$ CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC)=8/20/2/35/35 (by volume), and in place of adding propargyl 2,4-difluorobenzoate in Example C-1, propargyl 2-fluorobenzoate (Example C-2), propargyl 4-fluorobenzoate (Example C-3), allyl 2,4-difluorobenzoate (Example C-4), vinyl 2,4-difluorobenzoate (Example C-5), phenyl 2,4-difluorobenzoate (Example C-6), biphenyl 2,4-difluorobenzoate (Example C-7), propargyl 2,6-difluorobenzoate (Example C-8), propargyl 2,4,6-trifluorobenzoate (Example C-9), propargyl 2,3,4,6-tetrafluorobenzoate (Example C-10), or propargyl pentafluorobenzoate (Example C-11) was added thereto in an amount of 0.5% by weight, thereby preparing a nonaqueous electrolytic solution. Using this, a 18650-type cylindrical battery was constructed, and the battery characteristics were determined in the same manner as in Example C-1. The results are shown in Table C-1.

Examples C-12 to 15

LiPF$_6$ to be 0.95 M and LiN(SO$_2$ CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC)=8/20/2/35/35 (by volume); and propargyl 2,4-difluorobenzoate was added thereto in an amount of 0.01% by weight (Example C-12), 2% by weight (Example C-13), 5% by weight (Example C-14), or 10% by weight (Example C-15), thereby preparing a 18650-type cylindrical battery. In the same manner as in Example C-1, the battery characteristics were determined. The results are shown in Table C-1.

Example C-16

LiPF$_6$ to be 0.95 M and LiBF$_4$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC)=8/20/2/35/35 (by volume); and propargyl 2,4-difluorobenzoate was added thereto in an amount of 0.5% by weight, thereby preparing a 18650-type cylindrical battery. In the same manner as in Example C-1, the battery characteristics were determined. The results are shown in Table C-1.

Comparative Example C-1

LiPF$_6$ to be 0.95 M and LiN(SO$_2$ CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC)=8/20/2/35/35 (by volume), thereby preparing a nonaqueous electrolytic solution. Using this, a 18650-type cylindrical battery was constructed, and its battery characteristics were determined in the same manner as in Example C-1. The results are shown in Table C-1.

Comparative Examples C-2 to 5

LiPF$_6$ to be 0.95 M and LiN(SO$_2$ CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC)=8/20/2/35/35 (by volume), and in place of adding thereto propargyl 2,4-difluorobenzoate in Example C-1, methyl 2,4-difluorobenzoate (Comparative Example C-2), methyl 2,6-difluorobenzoate (Comparative Example C-3), methyl 2-fluorobenzoate (Comparative Example C-4), or methyl 4-fluorobenzoate (Comparative Example C-5) was added thereto in an amount of 0.5% by weight, thereby preparing a nonaqueous electrolytic solution. Using this, a 18650-type cylindrical battery was constructed, and its battery characteristics were determined in the same manner as in Example C-1. The results are shown in Table C-1.

TABLE C-1

| | Composition of Electrolyte Salt Composition of Nonaqueous Electrolytic Solution | Compound | Amount Added (wt. %) | Initial Efficiency (%) | Capacity Retention after 100 cycles (%) |
|---|---|---|---|---|---|
| Example C-1 | 0.95M LiPF$_6$ + 0.05M LiN(SO$_2$CF$_3$)$_2$ EC/PC/VC/MEC/DEC(8/20/2/35/35) | propargyl 2,4-difluorobenzoate | 0.5 | 85 | 85 |
| Example C-2 | 0.95M LiPF$_6$ + 0.05M LiN(SO$_2$CF$_3$)$_2$ EC/PC/VC/MEC/DEC(8/20/2/35/35) | propargyl 2-fluorobenzoate | 0.5 | 79 | 80 |
| Example C-3 | 0.95M LiPF$_6$ + 0.05M LiN(SO$_2$CF$_3$)$_2$ EC/PC/VC/MEC/DEC(8/20/2/35/35) | propargyl 4-fluorobenzoate | 0.5 | 77 | 79 |
| Example C-4 | 0.95M LiPF$_6$ + 0.05M LiN(SO$_2$CF$_3$)$_2$ EC/PC/VC/MEC/DEC(8/20/2/35/35) | allyl 2,4-difluorobenzoate | 0.5 | 86 | 84 |
| Example C-5 | 0.95M LiPF$_6$ + 0.05M LiN(SO$_2$CF$_3$)$_2$ EC/PC/VC/MEC/DEC(8/20/2/35/35) | vinyl 2,4-difluorobenzoate | 0.5 | 84 | 83 |
| Example C-6 | 0.95M LiPF$_6$ + 0.05M LiN(SO$_2$CF$_3$)$_2$ EC/PC/VC/MEC/DEC(8/20/2/35/35) | phenyl 2,4-difluorobenzoate | 0.5 | 81 | 83 |
| Example C-7 | 0.95M LiPF$_6$ + 0.05M LiN(SO$_2$CF$_3$)$_2$ EC/PC/VC/MEC/DEC(8/20/2/35/35) | biphenyl 2,4-difluorobenzoate | 0.5 | 80 | 80 |
| Example C-8 | 0.95M LiPF$_6$ + 0.05M LiN(SO$_2$CF$_3$)$_2$ EC/PC/VC/MEC/DEC(8/20/2/35/35) | propargyl 2,6-difluorobenzoate | 0.5 | 82 | 81 |
| Example C-9 | 0.95M LiPF$_6$ + 0.05M LiN(SO$_2$CF$_3$)$_2$ EC/PC/VC/MEC/DEC(8/20/2/35/35) | propargyl 2,4,6-trifluorobenzoate | 0.5 | 88 | 84 |
| Example C-10 | 0.95M LiPF$_6$ + 0.05M LiN(SO$_2$CF$_3$)$_2$ EC/PC/VC/MEC/DEC(8/20/2/35/35) | propargyl 2,3,4,6-tetrafluorobenzoate | 0.5 | 89 | 84 |
| Example C-11 | 0.95M LiPF$_6$ + 0.05M LiN(SO$_2$CF$_3$)$_2$ EC/PC/VC/MEC/DEC(8/20/2/35/35) | propargyl pentafluorobenzoate | 0.5 | 90 | 85 |
| Example C-12 | 0.95M LiPF$_6$ + 0.05M LiN(SO$_2$CF$_3$)$_2$ EC/PC/VC/MEC/DEC(8/20/2/35/35) | propargyl 2,4-difluorobenzoate | 0.01 | 79 | 80 |
| Example C-13 | 0.95M LiPF$_6$ + 0.05M LiN(SO$_2$CF$_3$)$_2$ EC/PC/VC/MEC/DEC(8/20/2/35/35) | propargyl 2,4-difluorobenzoate | 2 | 92 | 84 |
| Example C-14 | 0.95M LiPF$_6$ + 0.05M LiN(SO$_2$CF$_3$)$_2$ EC/PC/VC/MEC/DEC(8/20/2/35/35) | propargyl 2,4-difluorobenzoate | 5 | 93 | 80 |
| Example C-15 | 0.95M LiPF$_6$ + 0.05M LiN(SO$_2$CF$_3$)$_2$ EC/PC/VC/MEC/DEC(8/20/2/35/35) | propargyl 2,4-difluorobenzoate | 10 | 93 | 79 |
| Example C-16 | 0.95M LiPF$_6$ + 0.05M LiBF$_4$ EC/PC/VC/MEC/DEC(10/18/2/35/35) | propargyl 2,4-difluorobenzoate | 0.5 | 84 | 84 |
| Comparative Example C-1 | 0.95M LiPF$_6$ + 0.05M LiN(SO$_2$CF$_3$)$_2$ EC/PC/VC/MEC/DEC(8/20/2/35/35) | none | — | 25 | 0 |
| Comparative Example C-2 | 0.95M LiPF$_6$ + 0.05M LiN(SO$_2$CF$_3$)$_2$ EC/PC/VC/MEC/DEC(8/20/2/35/35) | methyl 2,4-difluorobenzoate | 0.5 | 67 | 57 |
| Comparative Example C-3 | 0.95M LiPF$_6$ + 0.05M LiN(SO$_2$CF$_3$)$_2$ EC/PC/VC/MEC/DEC(8/20/2/35/35) | methyl 2,6-difluorobenzoate | 0.5 | 65 | 55 |
| Comparative Example C-4 | 0.95M LiPF$_6$ + 0.05M LiN(SO$_2$CF$_3$)$_2$ EC/PC/VC/MEC/DEC(8/20/2/35/35) | methyl 2-fluorobenzoate | 0.5 | 33 | 23 |
| Comparative Example C-5 | 0.95M LiPF$_6$ + 0.05M LiN(SO$_2$CF$_3$)$_2$ EC/PC/VC/MEC/DEC(8/20/2/35/35) | methyl 4-fluorobenzoate | 0.5 | 20 | 15 |

Example C-17

LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/fluoroethylene carbonate (FEC)/vinylene carbonate (VC)/methyl ethyl carbonate (MEC)=3/20/5/2/70 (by volume); propargyl 2,4-difluorobenzoate in an amount of 0.5% by weight, adiponitrile in an amount of 1% by weight and cyclohexyl sulfite in an amount of 0.5% by weight were added thereto, thereby preparing a nonaqueous electrolytic solution and making a cylindrical battery in the same manner as in Example C-1. The battery characteristics were determined, and the results are shown in Table C-2.

Comparative Example C-6

Like in Example A-17, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/fluoroethylene carbonate (FEC)/vinylene carbonate (VC)/methyl ethyl carbonate (MEC)=3/20/5/2/70 (by volume); however, propargyl 2,4-difluorobenzoate, adiponitrile and cyclohexyl sulfite were not added thereto. Using the thus-prepared nonaqueous electrolytic solution, a cylindrical battery was constructed in the same manner as in Example C-17, and its battery characteristics were determined. The results are shown in Table C-2.

TABLE C-2

| | Composition of Electrolyte Salt Composition of Nonaqueous Electrolytic Solution | Compound | Amount Added (wt. %) | Initial Efficiency (%) | Capacity Retention after 100 cycles (%) |
|---|---|---|---|---|---|
| Example C-17 | 0.95M LiPF$_6$ + 0.05M LiN(SO$_2$CF$_3$)$_2$ EC/PC/FEC/VC/MEC(3/20/5/2/70) + adiponitrile (1 wt. %) + cyclohexyl sulfite (1 wt. %) | propargyl 2,4-difluorobenzoate | 0.5 | 93 | 86 |

TABLE C-2-continued

| | Composition of Electrolyte Salt Composition of Nonaqueous Electrolytic Solution | Compound | Amount Added (wt. %) | Initial Efficiency (%) | Capacity Retention after 100 cycles (%) |
|---|---|---|---|---|---|
| Comparative Example C-6 | 0.95M LiPF$_6$ + 0.05M LiN(SO$_2$CF$_3$)$_2$ EC/PC/FEC/VC/MEC(3/20/5/2/70) | none | — | 54 | 47 |

It is known that, as compared with the lithium secondary batteries of Comparative Examples not containing the specific compound represented by the general formula (III), the lithium secondary batteries of Examples C-1 to C-17 have more excellent battery performance in point of the initial battery capacity and the cycle property of the batteries.

Examples C-1 to C-17 of the present invention where the negative electrode is made of graphite confirm excellent cycle property; and not limited to the graphite negative electrode, the electrolytic solution of the present invention exhibits the same effects as in these Examples, for a silicon negative electrode, a tin negative electrode and an Li negative electrode, and also in a case where a lithium-containing olivine-type phosphate was used in the positive electrode.

INDUSTRIAL APPLICABILITY

According to the present invention, there are provided novel ester compounds useful as intermediate materials for medicines, agricultural chemicals, electronic materials, polymer materials and the like, or as battery materials.

The lithium secondary battery using the nonaqueous electrolytic solution of the present invention is excellent in the initial battery capacity and the cycle property thereof, and can maintain the battery performance for a long period of time.

The invention claimed is:

1. A nonaqueous electrolytic solution for a lithium secondary battery, the solution comprising an electrolyte dissolved in a nonaqueous solvent and an ester compound represented by formula (III) in an amount of from 0.01 to 10% by weight of the nonaqueous electrolytic solution:

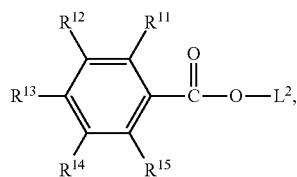

(III)

wherein:
$R^{11}$, $R^{13}$, $R^{14}$ and $R^{15}$ each independently represent a hydrogen atom or a fluorine atom;
$R^{12}$ represents a hydrogen atom, a fluorine atom, a methoxy group or an ethoxy group;
at least one of $R^{11}$ to $R^{15}$ is a fluorine atom;
$L^2$ represents an alkenyl group having from 2 to 6 carbon atoms, an alkynyl group having from 3 to 6 carbon atoms, or a biphenyl group.

2. The nonaqueous electrolytic solution of claim 1, wherein $L^2$ is a vinyl group, an allyl group or a propargyl group.

3. The nonaqueous electrolytic solution of claim 1, wherein at least two of $R^{11}$, $R^{13}$ and $R^{15}$ are fluorine atoms.

4. The nonaqueous electrolytic solution of claim 1, wherein the electrolytic solution further comprises at least two selected from the group consisting of ethylene carbonate, propylene carbonate, vinylene carbonate and fluoroethylene carbonate.

5. A lithium secondary battery, comprising a positive electrode, a negative electrode and a nonaqueous electrolytic solution of an electrolyte salt dissolved in a nonaqueous solvent, wherein the nonaqueous electrolytic solution comprises an ester compound of formula (III) in an amount of from 0.01 to 10% by weight of the nonaqueous electrolytic solution:

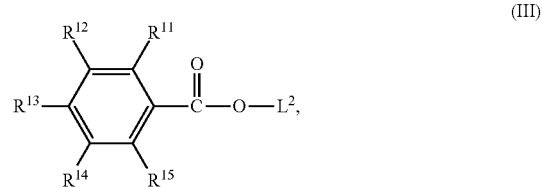

(III)

wherein:
$R^{11}$, $R^{13}$, $R^{14}$ and $R^{15}$ each independently represent a hydrogen atom or a fluorine atom;
$R^{12}$ represents a hydrogen atom, a fluorine atom, a methoxy group or an ethoxy group;
at least one of $R^{11}$ to $R^{15}$ is a fluorine atom;
$L^2$ represents an alkenyl group having from 2 to 6 carbon atoms, an alkynyl group having from 3 to 6 carbon atoms, or a biphenyl group.

* * * * *